United States Patent [19]
Uchida et al.

[11] Patent Number: 6,150,092
[45] Date of Patent: Nov. 21, 2000

[54] ANTISENSE NUCLEIC ACID COMPOUND TARGETED TO VEGF

[75] Inventors: Kiyoshi Uchida; Takayoshi Uchida; Youichi Tanaka; Yoko Matsuda; Shinichi Kondo, all of Tsukuba, Japan

[73] Assignee: Taogosei Company, Ltd., Tokyo, Japan

[21] Appl. No.: 08/765,340

[22] PCT Filed: Jun. 7, 1995

[86] PCT No.: PCT/JP95/01121

§ 371 Date: Dec. 23, 1996

§ 102(e) Date: Dec. 23, 1996

[87] PCT Pub. No.: WO96/00286

PCT Pub. Date: Jan. 4, 1996

[30] Foreign Application Priority Data

Jun. 27, 1994 [JP] Japan ................................. 6-145146
Nov. 21, 1994 [JP] Japan ................................. 6-311130

[51] Int. Cl.[7] .......................... C07H 21/04; C12Q 1/68; C12N 15/85
[52] U.S. Cl. ............................ 435/6; 435/91.1; 435/325; 536/23.1; 536/24.5
[58] Field of Search ................... 536/23.1, 24.5, 536/84.5; 514/44; 435/6, 91.1, 375, 325

[56] References Cited

U.S. PATENT DOCUMENTS

| | | | |
|---|---|---|---|
| 5,639,736 | 6/1997 | Robinson | 514/44 |
| 5,639,872 | 6/1997 | Robinson | 536/24.5 |
| 5,641,756 | 6/1997 | Robinson | 514/44 |
| 5,731,294 | 3/1998 | Robinson et al. | 514/44 |

FOREIGN PATENT DOCUMENTS

WO 95/04142  2/1995  WIPO.
WO 96/23065  1/1996  WIPO.

OTHER PUBLICATIONS

Tseng et al., Antisense oligonucleotide technology in the development of cancer therapeutics, Cancer Gene Therapy, vol. 1(1), pp. 65–71, Mar. 1994.

Gewirtz et al., Facility oligonucleotide delivery: helping antisense deliver on its promise, Proc. Natl. Acad. Sci., vol. 93, pp. 3161–3163, Apr. 1996

Rojanasakul et al., Antisense oligonucleotide therapeutics: drug delivery and targeting, Advenced Drug Delivery Reviews, vol. 18, pp. 115–131, 1996.

In: Antisense Res. Dev.; 5; Spring 95; 87–8; OP–10 Abstract and 1st International Antisense Conference in Japan; Dec. 4–7, 1994; "Selection of Antisense Oligodeoxyribonucleotides that Inhibit VEGF/VPF Expression in a Cell–free System."

*Primary Examiner*—George C. Elliott
*Assistant Examiner*—Andrew Wang
*Attorney, Agent, or Firm*—Morgan & Finnegan, L.L.P.

[57] ABSTRACT

The present invention relates to an antisense nucleic acid compound which has a nucleotide sequence complementary to at least 8 contiguous nucleotides in the nucleotide sequence of a gene coding for a vascular endothelial growth factor and which inhibits the expression of the vascular endothelial growth factor, as well as to a therapeutic or diagnostic agent for cancers, rheumatoid arthritis, diabetes etc., comprising said antisense nucleic acid as active ingredient. Further, the present invention relates to a method of preventing the expression of the vascular endothelial growth factor, comprising use of an antisense nucleic acid compound which has a nucleotide sequence complementary to at least 8 contiguous nucleotides in the nucleotide sequence of a gene coding for a vascular endothelial growth factor and which inhibits the expression of the vascular endothelial growth factor.

25 Claims, 12 Drawing Sheets

ANTISENSE NUCLEIC ACID COMPOUND TARGETED TO VEGF

FIELDS IN INDUSTRY

The present invention relates to an antisense nucleic acid compound which has a nucleotide sequence complementary to a nucleotide contained in the nucleotide sequence of a gene coding for a vascular endothelial growth factor and which inhibits the expression of the vascular endothelial growth factor (VEGF), as well as to uses thereof.

BACKGROUND OF THE INVENTION

Extensive research has conventionally been made of tumors and tumor cells as a basis of development of an anticancer drug. As a result, it was found that solid tumors need oxygen and nutrients supplied through blood vessels for their homeostasis in vivo, and without such blood vessels, they cannot be grown to 2 mm or more in diameter in vivo [Basic Science of Cancer, authored by I. F. Tannock and R. P. Hill and translated by Naoyuki Taniguchi, Medical Science International (1993); and "Hatsugan to Gan Saibo" (Carcinogenesis and Cancer Cells)], Cancer Bioscience 3, edited by Toshio Kuroki, Tokyo University Press (1991)).

For this arrival of blood vessels to solid tumors, it was proposed that solid tumor cells produce and secrete a certain factor (a tumor angiogenic factor) to induce blood vessels (J. Folkman, Annals of Surgery, Vol. 175, pp. 409–416 (1972)).

Recently, attention has been paid to a vascular endothelial growth factor as one of the substances which functions as a tumor angiogenic factor (N. Ferrara et al., Endocrine Reviews, Vol. 3, No. 1, pp. 18–31 (1992)). The vascular endothelial growth factor is the same substance as so-called "vascular permeability factor", and in some cases it is also called "vascular endothelial growth factor/vascular permeability factor". As such factor, 4 kinds of molecular species, which occur depending on the difference of splicing, are found in humans.

Recently, it has been found that this vascular endothelial growth factor does not exert direct action (e.g. growth promotion) on solid tumor cells in experiments with cells (in vitro). However, it has been found that this factor promotes the growth of solid tumors in experiments on with animals (in vivo). It has been further revealed that the growth of solid tumors is inhibited by administration of an anti-VEGF antibody to animals. These findings indicate that the vascular endothelial growth factor is a tumor angiogenic factor (K. J. Kim et al., Nature, Vol. 362, April 29 issue, pp. 841–844 (1993); S. Kondo et al., Biochemical and Biophysical Research Communications, Vol. 194, No. 3, pp. 1234–1241 (1933)).

From the foregoing, inhibition of the vascular endothelial growth factor leads to inhibition of growth of solid tumor cells, and this should be applicable in the development of anticancer agents. In fact there is a report on a method to use an anti-VEGF antibody. In this prior method, function of the vascular endothelial growth factor (i.e. function of facilitating the growth of solid tumors) biosynthesized via translation of mRNA is inhibited by the anti-VEGF antibody.

However, this prior method is based on the assumption that the vascular endothelial growth factor is present, so it is required for said factor which is not necessary to depress growth of tumor to be produced. Hence, this method cannot be effective until such substance is produced. Further, because the vascular endothelial growth factor itself is biosynthesized without special inhibition, this method is problematic if the specificity and binding ability of the anti-VEGF antibody is poor and the inhibitory action of the antibody is incomplete.

The object of the present invention is to provide a nucleic acid compound (i.e. antisense nucleic acid compound) which completely or almost completely inhibits expression of the vascular endothelial growth factor itself by inhibiting production of the vascular endothelial growth factors at the translation of mRNA, in place of inhibiting the action of the produced vascular endothelial growth factor by use of said anti-VEGF antibody.

SUMMARY OF THE INVENTION

To solve the problem, complementary nucleotides (i.e. antisense nucleic acid compounds) to a gene coding for the vascular endothelial growth factor were screened by using a transcription and translation system derived from a rabbit reticulocyte lysate. Among these, the present inventors found some complementary nucleotides effectively inhibiting the production of the vascular endothelial growth factor, and further confirmed their pharmacological effect on both cultured cells and experimental animals to complete the present invention.

Specifically, the present invention is antisense nucleic acid compounds having nucleotide sequences complementary to at least 8 contiguous nucleotides in the nucleotide sequence of the gene coding for the vascular endothelial growth factor, said antisense nucleic acid compound inhibiting the expression of the vascular endothelial growth factor.

The phrase "gene coding for the vascular endothelial growth factor" herein used means a structural gene defining the amino acid sequence of the vascular endothelial growth factor (including its signal peptide region), intervening sequences (introns) located in the structural gene, and upstream nucleotide sequences (promoter, operator etc.) and downstream nucleotide sequences (poly A etc.) involved in the expression of said gene. An example of this gene is shown in SEQ ID NO: 1.

Said antisense nucleic acid compounds include those compounds which inhibit the expression of the vascular endothelial growth factor to a level of 30% or less and more effectively to a level of 10% or less as compared to the expression in the absence of the compound. As those antisense nucleic acid compounds which inhibit the expression to a level of 10% or less, mention is made of an antisense nucleic acid compounds having a complementary sequence to at least 8 to 10 nucleotides in the nucleotide sequences of SEQ ID NOS:2 to 9. The effect of these antisense nucleic acid compounds can be confirmed in both cultured cell and experimental animal assay systems.

In addition, the present invention is a therapeutic agent comprising said antisense nucleic acid compound as active ingredient.

Further, the present invention is a diagnostic agent comprising said antisense nucleic acid compound as active ingredient.

Furthermore, the present invention is a method of inhibiting the expression of the vascular endothelial growth factor to a level of 30% or less, which comprises use of an antisense nucleic acid compound having a nucleotide sequence complementary to at least 8 contiguous nucleotides in the nucleotide sequence of the gene coding for the vascular endothelial growth factor.

The phrase "inhibit the expression of the vascular endothelial growth factor" herein used means that the vascular endothelial growth factor is not produced by interfering steps such as translation of mRNA coding step for said factor to produce the vascular endothelial growth factor.

DETAILED DESCRIPTION OF THE INVENTION

The antisense nucleic acid compound of the invention is obtained in the following manner by designing nucleic acid compounds on the basis of the concept of antisense nucleic acid and then evaluating their effect in terms of the amount of the vascular endothelial growth factor as the protein produced in their presence.

First, the gene which codes for the vascular endothelial growth factor (referred to hereinafter as "VEGF") is sequenced. Thereafter, a nucleic acid compound complementary to a partial nucleotide sequence in said gene is prepared by chemical synthesis etc. This compound is then evaluated by a screening test in a cell-free system whether it can effectively inhibit the production of VEGF or not. A nucleic acid compound having the nucleotide sequence found to inhibit the production of VEGF is the antisense nucleic acid compound of the invention.

In the present invention, if the above synthesized nucleic acid compound inhibits the expression of VEGF to a greater extent than a nucleic acid compound having a random nucleotide sequence, then said synthesized compound can be considered to effectively inhibit the expression. The "random nucleotide sequence" refers to a nucleotide sequence having not more than a statistically expected degree of complementation, and the "antisense nucleic acid compound" refers to a compound capable of inhibiting the expression of VEGF to 30% or less of that in the absence of the antisense nucleic acid compound.

The effect of some of such antisense nucleic acid compounds is evaluated by using cultured cells. For this, the antisense nucleic acid compounds which inhibit the expression of VEGF in a cell-free system for screening test are added to the VEGF-producing cells and the cells are cultured to determine whether the production of VEGF from said cultured cells is inhibited or not. The compounds whose effects were confirmed in this cultured cell system are further examined for their effect further in experimental animals.

(1) Construction of a plasmid

Before the gene coding for VEGF is sequenced, a plasmid capable of producing VEGF via transcription and translation in a cell-free system is constructed.

The preparation of a plasmid containing the structural gene of VEGF is not particularly limited. For example, it can be constructed as follows:

The upstream and downstream regions of a luciferase structural gene contained in plasmid pPoly(A)-luc(SP6) (Promega) are cleaved off respectively with restriction enzymes ApaI and SacI.

Separately, the VEGF structural gene can be prepared through cloning or isolated from e.g. a plasmid having said gene obtained through cloning. The VEGF structural gene may be derived from humans, bovines, guinea pigs, rats and mice, preferably humans.

The ApaI and SacI sites, which are respectively upstream and downstream of the VEGF structural gene, are cleaved with restriction enzymes ApaI and SacI, respectively. If said restriction sites are not present in the upstream and downstream regions of the VEGF structural gene thus obtained, then a DNA fragment containing said sites can be attached to the gene in a usual manner (J. Sambrook, E. F. Fritsch, T. Maniatis, Molecular Cloning: A Laboratory Manual, 2nd Ed., Gold Spring Harbor Laboratory Press, 1989).

The resulting fragment containing the VEGF structural gene is ligated to the above fragment of plasmid pPoly(A)-luc(SP6) from which the luciferase structural gene was removed with the 2 restriction enzymes. This ligation can be carried out using e.g. a DNA ligation kit available from Takara Shuzo Co., Ltd. The plasmid thus obtained may be introduced into E. coli etc. where the plasmid is replicated in a large amount as the E. coli is multiplied. E. coli JM109 available from Takara Shuzo Co., Ltd. can be used for this purpose.

Then, the desired plasmid is extracted from the E. coli in a usual manner for example as follows:

The cells of E. coli etc. containing the plasmid are harvested by centrifugation. Then, a GTE solution (50 mM glucose, 25 mM Tris-HCl, and 10 mM EDTA, pH 8.0) is added to the cells to obtain a cell-suspension, and the cells are lyzed with a mixture of a ⅕ volume of lysozyme solution (50 mg/ml) and a 20/9 volume of sodium hydroxide (0.2 N)-sodium dodecyl sulfate (1%) relative to the volume of the suspension. The solution is neutralized with potassium acetate (pH 5.2) (final concentration: 1M), and the insolubles present are removed by centrifugation. To remove the protein present, a mixture of phenol-chloroform-isoamyl alcohol (25:24:1) is added, and mixed with the sample. After centrifugation, the upper layer (aqueous layer) is transferred to a new tube, mixed with an equal volume of 2-propanol, and left for a while at room temperature. The sample is centrifuged to give a pellet containing the desired plasmid. The pellet is dissolved in a suitable amount of TE (10 mM Tris-HCl and 1 mM EDTA, pH 8.0), then mixed with solution for cesium chloride density-gradient centrifugation, and separated by ultracentrifugation. The cesium chloride can be removed by dialysis against TE (see Molecular Cloning supra).

The molecular weight of the plasmid thus obtained can be determined by agarose gel electrophoresis, polyacrylamide gel electrophoresis, pulsed field gel electrophoresis, gel filtration chromatography, sedimentation velocity method, light scattering method etc. The nucleotide sequence coding for VEGF can be determined by the Sanger method or Maxam-Gilbert method.

(2) Synthesis of nucleic acid compound

Then, nucleotide sequences each consisting of 8 to 30 contiguous nucleotides whose positions are 1 to 30 nucleotides apart from one another on the nucleotide sequence determined in (1) above are selected, and nucleic acid compounds complementary to the selected nucleotide sequences are synthesized. In a preferable method, nucleotide sequences each consisting of 10 to 20 contiguous nucleotides whose positions are 1 to 13 nucleotides apart from one other on the whole region of the nucleotide sequence coding for VEGF are selected, and nucleic acid compounds complementary to the selected nucleotide sequences are prepared by synthesis.

The nucleic acid compounds include natural-type oligodeoxyribonucleotides, phosphorothioate-type oligodeoxyribonucleotides, phosphorodithioate-type oligodeoxyribonucleotides, methylphosphonate-type oligodeoxyribonucleotides, phosphoramidate-type oligodeoxyribonucle otides, H-phosphonate-type oligodeoxyribonucleotides, triester-type oligodeoxyribonucleotides, α-anomer-type oligodeoxyribonucleotides, those oligoribonucleotide which correspond to said oligodeoxyribonucleotides, peptide nucleic acids, other artificial nucleic acids, and nucleic acid-modified compounds. Among these, the natural-type and phosphorothioate-type oligodeoxyribonucleotides are preferable because of their less nonspecific inhibition of expression, easiness of their synthesis etc. and because their hybrid (double-stranded chain) with mRNA can act as a substrate for RNase H.

The synthesis of the natural-type nucleic compound can be carried out with e.g. a 381A DNA synthesizer or 394 DNA/RNA synthesizer manufactured by ABI (Applied Biosystems Inc.) in accordance with the phosphoramidite method (see instructions available from ABI, or F. Eckstein, Oligonucleotides and Analogues: A Practical Approach, IRL Press (1991)).

In the phosphoramidite method, a nucleic acid-related compound is synthesized by condensation between the 3'-terminus of a modified deoxyribonucleoside or modified ribonucleoside and the 5'-terminus of another modified deoxyribonucleoside, modified ribonucleoside, oligomodified deoxyribonucleotide or oligo-modified-ribonucleotide by use of a reagent containing phosphoramidite protected with a cyanoethyl group etc.

The final cycle of this synthesis is finished to give a product with a protective group (dimethoxytrityl group etc.) bound to a hydroxyl group at the 5'-terminus of the sugar moiety. The oligomer thus synthesized at room temperature is cleaved off from the support, and its nucleotide and phosphate moieties are deprotected. In this manner, the natural-type oligonucleic acid compound is obtained in a crude form.

The phosphorothioate-type nucleic acid compound can also be synthesized in a similar manner to the above natural type by the phosphoramidite method with the synthesizer from ABI. The procedure after the final cycle of the synthesis is also the same as with the natural type.

The crude nucleic acid compound thus obtained can be purified in a usual manner e.g. ethanol precipitation, or reverse phase chromatography, ion-exchange chromatography and gel filtration chromatography in high performance liquid chromatography (HPLC), supercritical fluid chromatography, and it may be further purified by electrophoresis. A cartridge for reverse phase chromatography, such as tC18-packed SepPak Plus (long body/ENV) (Waters), can also be used.

The purification of the phosphorothioate-type nucleic acid compound (about 3 mg 20-nucleotides compound in a crude form) is carried out in a similar manner to the above natural type.

The purity of the natural-type and phosphorothioate-type nucleic acid compounds can be analyzed by HPLC.

The synthesized nucleic acid compound is used in screening as described below.

(3) Screening

The screening of the nucleic acid compound can be conducted by adding the nucleic acid compound synthesized in (2) above to a transcription and translation assay system in the presence of the VEGF-coding gene or to a translation system in the presence of mRNA transcribed from said gene to examine its inhibition of the expression of VEGF in the system.

This reaction is carried out usually at a temperature of 25 to 40° C. over a period of 0.5 to 3 hours, preferably at 30° C. for 1 to 2 hours or at 37° C. for 1 hour.

Hereinafter, a method for expressing the protein (VEGF) is described below using a plasmid having the VEGF-coding gene.

Any expression vector containing the VEGF structural gene and being capable of expressing said gene can be used in a usual manner. The transcription and translation system permitting the VEGF structural gene to be expressed for production of VEGF includes that transcription and translation system which is derived from a rabbit reticulocyte lysate or wheat germ extract.

Preferably the expression system makes use of plasmid pSU02. In this case, a transcription and translation system derived from a rabbit reticulocyte lysate, available from Promega, can be used. A kit of TNT™ SP6 Coupled Reticulocyte Lysate System available from Promega is suitable in the case of transcription and translation with pSU02, because an SP6 promoter is located upstream to the VEGF structural gene in plasmid pSU02. The experiment can be conducted according to the manufacture's instructions attached to this kit.

To confirm the formation of VEGF in this transcription and translation system, two methods may be used.

The first method is sandwich-type enzyme linked immunoassays (see e.g. E. Harlow, D. Lane, Antibodies: A Laboratory Manual, Cold Spring Harbor Laboratory (1988)) using anti-VEGF polyclonal antibodies obtained from a rabbit which was previously administered with human-derived VEGF and produced in E. coli (see S. Kondo et al., Biochemical and Biophysical Research Communications, Vol. 194, No. 3, pp. 1234–1241 (1993)).

This generally well-known method is carried out as follows: The anti-VEGF polyclonal antibodies obtained as described above are immobilized onto a microtiter plate in a usual manner (see e.g. E. Harlow and D. Lane, Antibodies: A Laboratory Manual, supra). The VEGF-coding gene is added to a transcription and translation assay system and incubated at a suitable temperature for a suitable period. This reaction mixture is added to each well of the microtiter plate. The plate was left at room temperature and then washed. Other anti-VEGF polyclonal antibodies previously labeled with horseradish peroxidase are added to each well, left at room temperature, and washed. An orthodiaminobenzene solution is added thereto as substrate and left at room temperature until suitable coloration takes place. The absorbance of the solution is determined to estimate the content of VEGF.

The second method makes use of SDS-PAGE (sodium dodecyl sulfate-polyacrylamide gel electrophoresis) and autoradiography to confirm the formation of VEGF in said transcription and translation system.

SDS-PAGE may be carried out in a usual manner (see e.g. the manufacturer's instructions attached to the transcription and translation system kit available from Promega; and Toshio Takagi: "PAGE Polyacrylamide Gel Denkieidoho" (PAGE Polyacrylamide Gel Electrophoresis), published by Hirokawa Shoten K. K. (1990)). A typical example is as follows.

A 2-mercaptoethanol-containing SDS sample buffer in accordance with the instructions of Promega is added to the reaction mixture in the transcription and translation system, then sealed and thermally treated to denature the protein present. This sample is added to each well on a sodium dodecyl sulfate-polyacrylamide gel attached to an electrophoresis chamber and electrophoresed in the gel (15% or 17.5% polyacrylamide gel). To conduct autoradiography, the gel is transferred to a filter paper, dried in an oven, laid on X-ray film in the dark to be introduced into a cassette and left at room temperature over a period of a few hours to tens of hours until the X-ray film is exposed and then the film is developed. If the VEGF-coding gene was expressed, a band appears at a position corresponding to the molecular weight of VEGF. If the expression of said gene was inhibited by the antisense nucleic acid compound, said band does not appear or weakly appears. The position of said band varies depending on the difference of the gene contained in the plasmid used. For example, the band appears at a molecular weight of about 15 kd if pSU02 was used as plasmid, while the band appears at a molecular weight of about 60 kd if pPoly(A)-luc(PS6) was used as plasmid.

RNase H can also be added to the system to improve the inhibitory effect of the antisense nucleic acid compound on the expression of the VEGF-coding gene. RNase H is an enzyme which cleaves mRNA, produced by transcription of DNA, at sites where mRNA forms double strands via hydrogen bonding with DNA having complementary nucleotide sequence with mRNA. (H. Stein and P. Hausen, Science, Vol. 166, pp. 393 to 395 (1969); P. Hausen and H. Stein, European Journal of Biochemistry, Vol. 14, pp. 278 to 283 (1970)). By the action of this enzyme, the production of the protein encoded by this gene is inhibited more reliably.

If the natural-type oligodeoxyribonucleotide is used, the concentration of the antisense nucleic acid compound ranges from 0.1 to 10 $\mu$M, preferably 0.4 to 2 $\mu$M. More preferably the concentration is 0.4 $\mu$M in the coexistence of RNaseH. If the phosphorothioate-type oligodeoxyribonucleotide is used, the concentration of the antisense nucleic acid compound ranges from 0.01 to 1 $\mu$M, preferably 0.02 to 0.4 $\mu$M. More preferably the concentration is 0.064 to 0.15 $\mu$M in the coexistence of RNaseH.

The inhibitory effect of the added nucleic acid compound (i.e. antisense nucleic acid compound) on the expression of the VEGF-coding gene can be evaluated by making a comparison with the expression in the absence of the compound. Specifically, the produced VEGF can be subjected to e.g. SDS-PAGE and then autoradiography as described above to determine the density with a densitometer, where the density in the presence of the antisense nucleic acid compound is compared with the density in the absence of the compound.

The degree of inhibition of the expression of the gene can thus be determined.

To inhibit expression of the gene, the nucleic acid compound has a nucleotide sequence complementary to at least 8 nucleotides, preferably contiguous 8 nucleotides, more preferably at least 14 nucleotides. If one mismatched nucleotide is contained, the nucleic acid compound to inhibit expression of the gene has at least 8 complementary nucleotides, preferably has at least 5 contiguous nucleotide sequence as its shorter contiguous sequence interrupted by said mismatched nucleotide and also has 11 or more complementary nucleotides in total. The number of nucleotides is not limited within these ranges. Although a nucleotide sequence complementary to 30 or more nucleotides may be used, no further improvement can be achieved and it is difficult to synthesize such a long sequence, so the nucleic acid compound having a nucleotide sequence complementary to 30 or less nucleotides suffices to achieve the object of the present invention.

The antisense nucleic acid compound thus obtained is useful as a therapeutic agent to inhibit the growth of solid tumor cells or treat rheumatoid arthritis and diabetes, or as a diagnostic agent for cancers and other diseases.

If the antisense nucleic acid compound of the present invention is used as a therapeutic agent, the object of administration is not particularly limited. For example, the object of administration may be to prevent or treat various kinds of cancer. The compound may be administered orally or parenterally. The oral administration includes sublingual administration. The parenteral administration includes injection (e.g. intracutaneous, intramuscular, intravenous, intra-arterial injection), infusion, suppository, ointment, poultice etc. The dose can be varied within a wide range depending on the subject (animal or human), age, administration route, intervals of administration. The dose of the effective antisense nucleic acid compound itself presented in the present invention or the dose of the antisense nucleic acid compound used with a suitable diluent or with a pharmacologically acceptable carrier ranges from 1 to 80,000 $\mu$g/kg body weight/day, and is administered successively or once or in portions per day.

Tablets, granules, powder, capsules etc., in the case of oral administration of the antisense nucleic acid compound of the invention, contain customary additives such as binders, fillers, lubricants, disintegrator, wetting agent etc. Liquid preparations for oral administration may be in the form of oral aqueous agent, suspension, emulsion, syrup etc. A dried product may also be used which is dissolved before use. The composition may further contain any additives and preservatives.

In the case of parenteral administration, the preparation contains additives such as stabilizer, buffer, preservative, isotonic agent etc., usually in an ampoule for single administration, a vessel for multiple administrations or in a tube. The composition may be powder to be dissolved in suitable liquid e.g. pyrogen-free sterilized water.

The antisense nucleic acid compound of the invention can be used as a diagnostic agent for e.g. cancer. Because it is known that cancer cells generally produce VEGF, cancer cells can be diagnosed by examining the degree of expression of VEGF in cells with a probe that is the nucleic acid compound of the invention having a nucleotide sequence complementary to a specific nucleotide sequence in the VEGF-coding gene or its transcribed mRNA.

(4) Effect of the antisense nucleic acid in cultured cell and experimental animal assay systems A pharmacological test is carried out in the following manner to evidence that the antisense nucleic acid compound of the invention is useful as a therapeutic or diagnostic agent.

A natural-type oligodeoxyribonucleotide or phosphorothioate-type oligodeoxyribonucleotide expected to have a nucleotide sequence with the antisense nucleic acid effect is used as the antisense nucleic acid compound to evaluate its effect on the expression of VEGF in a cultured cell system, as follows: The antisense nucleic acid compound such as natural-type oligodeoxyribonucleotide or phosphorothioate-type oligodeoxyribonucleotide is added at a concentration of 0.01 to 100 $\mu$M, preferably 0.1 to 10 $\mu$M, to cells derived mammals such as human, mouse, rat, guinea pig, bovine etc. under germ-free conditions, if necessary in the presence of reagents facilitating incorporation of antisense nucleic acid compound into cells, such as a lipofectin reagent, lipofectamine reagent, DOTAP reagent, artificial synthetic lipid vehicle, liposome, membrane fusion reagent, polymeric micellar reagent, polymeric carrier etc. The inhibition of the expression of the target protein (VEGF) can then be evaluated by e.g. ELISA (enzyme-linked immunoassay) or Western blotting using anti-VEGF antibody to confirm the inhibitory effect of the antisense nucleic acid compound on the expression of the protein.

A natural-type oligodeoxyribonucleotide or phosphorothioate-type oligodeoxyribonucleotide having a nucleotide sequence of expected antisense effect is used as the antisense nucleic acid compound to evaluate its effect on the expression of VEGF in an experimental animal system, as follows: The antisense nucleic acid compound such as natural-type oligodeoxyribonucleotide or phosphorothioate-type oligodeoxyribonucleotide is administered at a dose of 0.001 to 100 mg/kg body weight, preferably 0.1 to 80 mg/kg body weight, into mammals such as mouse, rat, guinea pig, rabbit etc., if necessary together with drug delivery system reagents, such as a lipofectin reagent, lipofectamine reagent, DOTAP reagent, artificial synthetic lipid vehicle, liposome, membrane fusion reagent, polymeric micellar reagent, polymeric carrier etc. via intravenous injection, intra-arterial injection, intracutaneous injection, intraperitoneal administration, or topical administration. The inhibition of the expression of the target protein (VEGF) can then be evaluated by e.g. ELISA or Western blotting using anti-VEGF antibody to confirm the inhibitory effect of the antisense nucleic acid on the expression of the protein. Further, human-derived cancer cells etc. can also be transplanted to animals such as mouse, rat, guinea pig and rabbit to evaluate the effect of the antisense nucleic acid compound such as natural-type oligodeoxyribonucleotide or phosphorothioate-type oligodeoxyribonucleotide on the growth of said cells. In this case, too, the antisense nucleic acid compound is administered at a dose of 0.001 to 100 mg/kg body weight, preferably 0.1 to 80 mg/kg body weight into the animals, if necessary together with drug delivery system reagents, such as a lipofectin reagent, lipofactamine reagent, DOTAP reagent, artificial synthetic lipid vehicle, liposome, membrane fusion reagent, polymeric micellar reagent, polymeric carrier etc. via intravenous injection, intra-arterial injection, intracutaneous injection, intraperitoneal administration, or topical administration. On the basis of the degree of inhibition of cancer cell growth by the antisense nucleic acid compound and the number of survival days of the experimental animals, the antisense nucleic acid effect can be evaluated.

Specific examples of such tests will be described below.

BEST MODE FOR CARRYING OUT THE INVENTION

The present invention is described in more detail by referring to the following examples, which however are not intended to limit the scope of the present invention.

EXAMPLE 1

(1) Construction and sequencing of the plasmid

The upstream and downstream regions of a luciferase structural gene contained in plasmid pPoly(A)-luc(SP6) (Promega) were cleaved off with restriction enzymes ApaI and SacI, respectively. Separately, a gene coding for human-derived VEGF obtained by the PCR method was inserted into a region between ApaI and XbaI sites in a multicloning site in plasmid pRC/CMV, whereby plasmid pSU01 was constructed, and then its upstream ApaI site and downstream SacI site were cleaved with restriction enzymes ApaI and SacI, respectively.

Using a DNA ligation kit available from Takara Shuzo Co., Ltd., the above ApaI- and SacI-cleaved fragment containing the VEGF structural gene was ligated to the above pPoly(A)-luc(SP6) fragment from which the luciferase structural gene had been removed with the 2 restriction enzymes ApaI and SacI (the ligation method followed the manufacture's instructions).

Then, the plasmid thus obtained was introduced into E. coli competent cell JM109 available from Takara Shuzo Co., Ltd. according to the manufacture's instructions and then replicated in a large amount. The E. coli cells carrying the plasmid were harvested by centrifugation. A GTE solution (50 mM glucose, 25 mM Tris-HCl, and 10 mM EDTA, pH 8.0) was added to the cells to prepare a suspension, and the cells were lysed with a mixture of a ⅛ volume of lysozyme solution (50 mg/ml) and a 20/9 volume of sodium hydroxide (0.2 N)-sodium dodecyl sulfate (1%) relative to the volume of the suspension. The solution was neutralized with potassium acetate (pH 5.2) (final concentration: 1M), and the insolubles present were removed by centrifugation. To remove the protein present, a mixture of phenol-chloroform-isoamyl alcohol (25:24:1) was added and mixed with the sample. After centrifugation, the upper layer (aqueous layer) was transfered to a new tube, mixed with an equal volume of 2-propanol, and left for a while at room temperature. The sample was centrifuged to give a pellet containing the desired plasmid (designated pSU02). The pellet was dissolved in a suitable amount of TE (10 mM Tris-HCl and 1 mM EDTA, pH 8.0), then mixed with solution for cesium chloride density-gradient centrifugation, and separated by ultracentrifugation. The resulting plasmid was dialyzed against TE to remove the cesium chloride (see Molecular Cloning supra). The desired plasmid (pSU02), 0.7 mg, was thus obtained.

Figure 1:
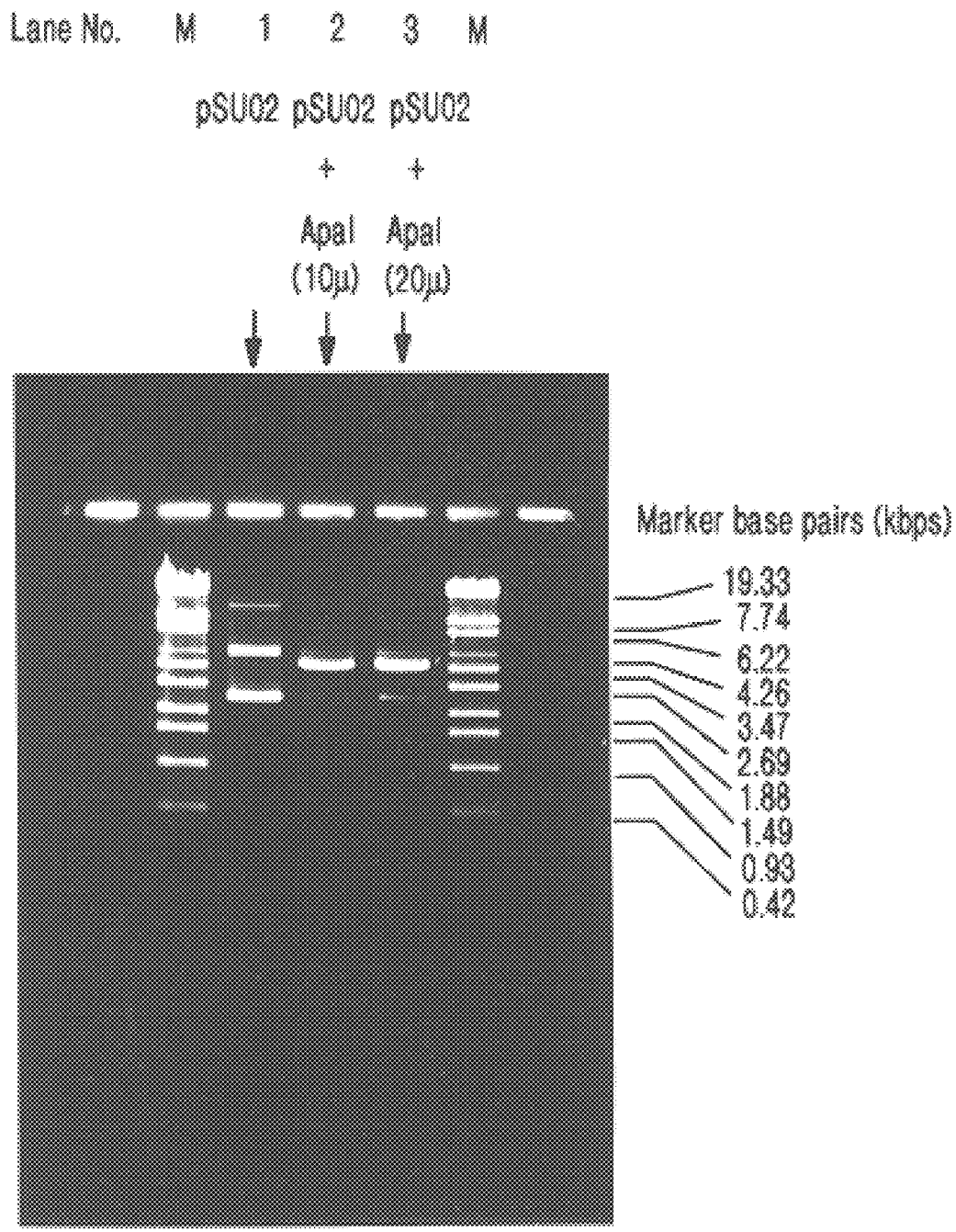
FIG. 1 shows the result of agarose gel electrophoresis for the plasmid (pSU02). In this photograph, lane 1 shows pSU02 only; lane 2, pSU02 treated with restriction enzyme ApaI (10 U); and lane 3, pUS02 treated with restriction enzyme ApaI (20 U). M shows a molecular weight marker.

Agarose gel electrophoresis indicated that this plasmid (pSU02) was about 3.6 kbp long (FIG. 1). In FIG. 1, lane 1 shows pSU02 only; lane 2, pUS02 treated with restriction enzyme ApaI (10 U); and lane 3, pUS02 treated with restriction enzyme ApaI (20 U). M shows a molecular weight marker.

Then, the nucleotide sequence of the VEGF structural gene including its surrounding regions in plasmid pSU02 was determined by the Sanger method. The nucleotide sequence thus determined is shown in SEQ ID NO:1.

(2) Synthesis and purification of natural-type and phosphorothioate-type nucleic acid compounds Nucleotides whose sequences were complementary to 20 contiguous nucleotides that are 6 nucleotide apart from one another between the 77-position and the 570-position in SEQ ID NO:1 were synthesized in 381A DNA synthesizer or 394 DNA/RNA synthesizer manufactured by ABI by the phosphoramidite method in accordance with the manufacture's instructions. Eighty nucleotides thas obtained are shown in Table 1, i.e. A077 to A551 (SEQ ID NOS:12–91, respectively). Five nucleic acid compounds each consisting of 20 nucleotides, i.e. S101 to T-20 (SEQ ID NOS:92–96, respectively) shown in Table 1 and 77 nucleic acid compounds each consisting of 6 to 18 nucleotides in Table 2 were also synthesized in a similar manner. The final cycle of this synthesis was finished to give a product with a protective group (dimethoxytrityl group) bound to the 5'-terminal hydroxyl group of its sugar moiety. At room temperature, the synthesized oligomer was cleaved off from the support by treatment with about 25% ammonium water for 60 minutes. The product was kept at 55° C. for 8 hours to deprotect its base and phosphate moieties.

In this manner, the natural-type oligodeoxyribonucleotides were obtained in crude form.

Each of the crude natural-type oligodeoxyribonucleotides was purified through a cartridge, SepPak Plus (long body/ ENV packed with tC18, manufactured by Waters) for reverse phase chromatography, as follows:

The inside of the cartridge was washed with 20 ml acetonitrile and then equilibrated with 20 ml of 12% acetonitrile-88% TEAA (TEAA: 0.1M triethyl ammonium acetate, pH 7.2). The crude oligodeoxyribonucleotide was dissolved in about 3 ml of 12% acetonitrile-88% TEAA and injected into the cartridge, and the elute flowed out in this injection was returned to the cartridge by injection, and the same procedure was repeated again. After the cartridge was washed with 15 ml of 12% acetonitrile-88% TEAA, the solution in the cartridge was replaced by 3 ml TEAA. Then, 3 ml of 2% aqueous trifluoroacetic acid was injected into the cartridge and left for about 4 minutes to cleave off the dimethoxytrityl group. Additional 3 ml of 2% aqueous trifluoroacetic acid was injected to push out the previous aqueous trifluoroacetic acid from the cartridge. The inside of the cartridge was replaced by 3 ml TEAB (triethylammonium bicarbonate, pH 7) and the sample was eluted with 8 ml of 15% acetonitrile-85% TEAB. The fractions containing the purified oligodeoxyribonucleotide were collected and evaporated into dryness under reduced pressure. 0.2 ml sterilized physiological saline was added to this sample, and it was evaporated into dryness again under reduced pressure. A small amount of sterilized water was added to this sample and it was evaporated again, and this procedure was repeated. Then, the same amount of sterilized water as the initially added physiological saline was added to the sample, and it was diluted to a predetermined concentration (500 µM oligodeoxyribonucleotide) and used in the screening experiment described below. For evaluation of the amount of the nucleic acid compound, it was assumed that 33 µg oligodeoxyribonucleotide in 1 ml buffer (20 mM sodium phosphate buffer, 100 mM NaCl, pH 7.0) has an absorbance of 1 at 260 nm as determined at room temperature in a cuvette of 1 cm light path length, and that the molecular weight of the natural-type oligodeoxyribonucleotide per nucleotide is 330. Alternatively, the amount of the nucleic acid compound was determined at 70 to 80° C. according to the nearest-neighbor approximation method on the basis of the reported molecular absorption coefficients of mononucleotide and dinucleotide (E. G. Richards, Handbook of Biochemistry and Molecular Biology: Nucleic Acids (edited by C. D. Fasman), 3rd ed., vol. I, p. 197, CRC Cleveland, Ohio). The concentrations of the nucleic acid compounds described in the present specification were determined in any of the above methods.

The purification of the crude phosphorothioate-type oligodeoxyribonucleotide (about 3 mg crude product of 20 nucleotides) was also carried out in a similar manner to the above natural type except that 20% acetonitrile-80% TEAA (or TEAB) was used in equilibrating the cartridge, washing the cartridge after application of the crude sample, and eluting the purified phosphorothioate-type oligodeoxyribonucleotide.

The nucleotide sequences of the natural-type deoxyribonucleotides synthesized are shown in Tables 1 and 2.

TABLE 1

| sample # | nucleotide sequence 5'← →3' | expression (%) | SEQ. ID NO. |
|---|---|---|---|
| A077 | TCGGAGGCCCGACCGGGGCC | 100 | 12 |
| A083 | ATGGTTTCGGAGGCCCGACC | 37 | 13 |
| A089 | AAGTTCATGGTTTCGGAGGC | 6 | 14 |
| A095 | AGCAGAAAGTTCATGGTTTC | 6 | 15 |
| A101 | CAAGACAGCAGAAAGTTCAT | 25 | 16 |
| A107 | TGCACCCAAGACAGCAGAAA | 16 | 17 |
| A113 | CTCCAATGCACCCAAGACAG | 16 | 18 |
| A119 | GCAAGGCTCCAATGCACCCA | 14 | 19 |
| A125 | AGCAAGGCAAGGCTCCAATG | 18 | 20 |
| A131 | TAGAGCAGGAAGGCAAGGCT | 28 | 21 |
| A137 | TGGAGGTAGAGCAGGAAGGC | 21 | 22 |
| A143 | GCATGGTGGAGGTAGAGCAG | 0 | 23 |
| A149 | CACTTGGCATGGTGGAGGTA | 4 | 24 |
| A155 | TGGGACCACTTGGCATGGTG | 9 | 25 |
| A161 | GCAGCCTGGGACCACTTGGC | 3 | 26 |
| A167 | ATGGGTGCAGCCTGGGACCA | 37 | 27 |
| A173 | TCTGCCATGGGTGCAGCCTG | 67 | 28 |
| A179 | CCTCCTTCTGCCATGGGTGC | 5 | 29 |
| A185 | TGCCCTCCTCCTTCTGCCAT | 5 | 30 |
| A191 | TGATTCTGGCCTCCTCCTTC | 7 | 31 |
| A197 | TCGTGATGATTCTGCCCTCC | 0 | 32 |
| A203 | ACCACTTCGTGATGATTCTG | 13 | 33 |
| A209 | AACTTCACCACTTCGTGATG | 29 | 34 |
| A215 | TCCATGAACTTCACCACTTC | 11 | 35 |
| A221 | TAGACATCCATGAACTTCAC | 18 | 36 |
| A227 | CGCTGATAGAGATCCATGAA | 3 | 37 |
| A233 | TAGCTGCGCTGATAGACATC | 23 | 38 |
| A239 | TGGCAGTAGCTGCGCTGATA | 43 | 39 |
| A245 | ATTGGATGGCAGTAGCTGCG | 50 | 40 |
| A251 | GTCTCGATTGGATGGCAGTA | 0 | 41 |
| A257 | ACGAGGGTCTCGATTGGATG | 3 | 42 |
| A263 | ATGTCCACCAGGGTCTCGAT | 1 | 43 |
| A269 | TGGAAGATGTCCACCAGGGT | 46 | 44 |
| A275 | TACTCCTGGAAGATGTCCAC | 16 | 45 |
| A281 | TCAGGGTACTCCTGGAAGAT | 1 | 46 |
| A287 | ATCTCATCAGGGTACTCCTG | 1 | 47 |
| A293 | TACTCGATCTCATCAGGGTA | 12 | 48 |
| A299 | AAGATGTACTCGATCTCATC | 0 | 49 |
| A305 | GGCTTGAAGATGTACTCGAT | 0 | 50 |
| A311 | CAGGATGGCTTGAAGATGTA | 4 | 51 |
| A317 | GGCACACAGGATGGCTTGAA | 11 | 52 |
| A323 | ATCAGGGCACACAGGATGG | 23 | 53 |
| A329 | CATCGCATCAGGGCACACA | 51 | 54 |
| A335 | CCCCCGCATCGCATCAGGGG | 58 | 55 |
| A341 | CAGCAGCCCCCGCATCGCAT | 39 | 56 |
| A347 | TCATTGCAGCAGCCCCCGCA | 9 | 57 |

TABLE 1-continued

| sample # | nucleotide sequence 5'← →3' | expression (%) | SEQ. ID NO. |
|---|---|---|---|
| A353 | CCCTCGTCATTGCAGCAGCC | 1 | 58 |
| A359 | TCCAGGCCCTCGTCATTGCA | 0 | 59 |
| A365 | ACACACTCCAGGCCCTCGTC | 14 | 60 |
| A371 | GTGGGCACACACTCCAGGCC | 35 | 61 |
| A377 | TCCTCAGTGGGCACACACTC | 28 | 62 |
| A383 | TTGGACTCCTCAGTGGGCAC | 6 | 63 |
| A389 | GTGATGTTGGACTCCTCAGT | 0 | 64 |
| A395 | TGCATGGTGATGTTGGACTC | 0 | 65 |
| A401 | ATAATCTGCATGGTGATGTT | 0 | 66 |
| A407 | ATCCGCATAATCTGCATGGT | 0 | 67 |
| A413 | GGTTTGATCCGCATAATCTG | 0 | 68 |
| A419 | TGGTGAGGTTTGATCCGCAT | 0 | 69 |
| A425 | TGGCCTTGGTGAGGTTTGAT | 0 | 70 |
| A431 | ATGTGCTGGCCTTGGTGAGG | 0 | 71 |
| A437 | TCTCCTATGTGCTGGCCTTG | 0 | 72 |
| A443 | CTCATCTCTCCTATGTGCTG | 0 | 73 |
| A449 | AGGAAGCTCATCTCTCCTAT | 0 | 74 |
| A455 | TGCTGTAGGAAGCTCATCTC | 0 | 75 |
| A461 | TTGTTGTGCTGTAGGAAGCT | 0 | 76 |
| A467 | TCACATTTGTTGTGCTGTAG | 3 | 77 |
| A473 | CTGCATTCACATTTGTTGTG | 0 | 78 |
| A479 | TTTGGTCTGCATTCACATTT | 0 | 79 |
| A485 | TCTTTCTTTGGTCTGCATTC | 0 | 80 |
| A491 | GCTCTATCTTTCTTTGGTCT | 0 | 81 |
| A497 | TGTCTTGCTCTATCTTTCTT | 0 | 82 |
| A503 | TTTTCTTGTCTTGCTCTATC | 0 | 83 |
| A509 | TCACATTTTCTTGTCTTGC | 0 | 84 |
| A515 | GGCTTGTCACATTTTTCTTG | 0 | 85 |
| A521 | CGCCTCGGCTTGTCACATTT | 0 | 86 |
| A527 | GCTCACCGCCTCGGCTTGTC | 37 | 87 |
| A533 | TGCCCGGCTCACCGCCTCGG | 64 | 88 |
| A539 | TCCTCCTGCCCGGCTCACCG | 11 | 89 |
| A545 | GCTCCTTCCTCCTGCCCGGC | 0 | 90 |
| A551 | AGGGAGGCTCCTTCCTCCTG | 68 | 91 |
| S101 | ATGAACTTTCTGCTGTCTTG | 44 | 92 |
| RA101 | AACTATAAGCACGGTAACGA | 66 | 93 |
| RA143 | GAAGTGAGCGTGAGCGTGAG | 57 | 94 |
| RS143 | CTCACGCTCACGCTCACTTC | 38 | 95 |
| T-20 | TTTTTTTTTTTTTTTTTTTT | 70 | 96 |

TABLE 2

| sample # | nucleotide sequence 5'← →3' | expression (%) | SEQ. ID NO. |
|---|---|---|---|
| A083N | TCGGAGGCCCGACC | 46 | 97 |
| A085N | TTTCGGAGGCCCGA | 37 | 98 |
| A085R | ATGGTTTCGGAGGCCCGA | 6 | 99 |
| A087P | ATGGTTTCGGAGGCCC | 7 | 100 |
| A089N | ATGGTTTCGGAGGC | 1 | 101 |
| A095N | AAGTTCATGGTTTC | 0 | 102 |
| A101N | AGCAGAAAGTTCAT | 8 | 103 |
| A105N | AGACAGCAGAAAGT | 18 | 104 |
| A108N | CCAAGACAGCAGAA | 23 | 105 |
| A109N | CCCAAGACAGCAGA | 18 | 106 |
| A110N | ACCCAAGACAGCAG | 25 | 107 |
| A143N | TGGAGGTAGAGCAG | 17 | 108 |
| A146N | TGGTGGAGGTAGAG | 5 | 109 |
| A153N | CTTGGCATGGTGGA | 1 | 110 |
| A155N | CACTTGGCATGGTG | 3 | 111 |
| A156N | CCACTTGGCATGGT | 5 | 112 |
| A157N | ACCACTTGGCATGG | 17 | 113 |
| A167N | GCAGCCTGGGACCA | 2 | 114 |
| A173N | ATGGGTGCAGCCTG | 29 | 115 |
| A176N | GCCATGGGTGCAGC | 12 | 116 |
| A179N | TCTGCCATGGGTGC | 1 | 117 |
| A189N | CCCTCCTCCTTCTG | 0 | 118 |
| A191N | TGCCCTCCTCCTTC | 1 | 119 |
| A193N | TCTGCCCTCCTCCT | 0 | 120 |
| A203N | TCGTGATGATTCTG | 0 | 121 |
| A209N | ACCACTTCGTGATG | 11 | 122 |
| A213N | CTTCACCACTTCGT | 2 | 123 |
| A217N | TGAACTTCACCACT | 4 | 124 |

TABLE 2-continued

| sample # | nucleotide sequence 5'← →3' | expression (%) | SEQ. ID NO. |
|---|---|---|---|
| A237N | GCTGCGCTGATAGA | 2 | 125 |
| A242N | CAGTAGCTGCGCTG | 11 | 126 |
| A245N | TGGCAGTAGCTGCG | 19 | 127 |
| A248N | GGATGGCAGTAGCT | 2 | 128 |
| A251N | ATTGGATGGCAGTA | 0 | 129 |
| A261N | CAGGGTCTCGATTG | 0 | 130 |
| A263N | ACCAGGGTCTCGAT | 0 | 131 |
| A265N | CCACCAGGGTCTCG | 10 | 132 |
| A275N | TGGAAGATGTCCAC | 85 | 133 |
| A293N | ATCTCATCAGGGTA | 8 | 134 |
| A296N | TCGATCTCATCAGG | 9 | 135 |
| A299N | TACTCGATCTCATC | 9 | 136 |
| A303N | GATGTACTCGATCT | 1 | 137 |
| A313N | ATGGCTTGAAGATG | 3 | 138 |
| A317N | CAGGATGGCTTGAA | 4 | 139 |
| A319N | CACAGGATGGCTTG | 21 | 140 |
| A321N | CACACAGGATGGCT | 9 | 141 |
| A323N | GGCACACAGGATGG | 38 | 142 |
| A325N | GGGGCACACAGGAT | 51 | 143 |
| A347N | CAGCAGCCCCCGCA | 37 | 144 |
| A351N | ATTGCAGCAGCCCC | 24 | 145 |
| A356N | TCGTCATTGCAGCA | 0 | 146 |
| A361N | GGCCCTCGTCATTG | 0 | 147 |
| A365N | TCCAGGCCCTCGTC | 2 | 148 |
| A368N | CACTCCAGGCCCTC | 33 | 149 |
| A371N | ACACACTCCAGGCC | 41 | 150 |
| A379R | TCCTCAGTGGGCACACAC | 45 | 151 |
| A381P | TCCTCAGTGGGCACAC | 35 | 152 |
| A383N | TCCTCAGTGGGCAC | 4 | 153 |
| A397N | TGGTGATGTTGGAC | 0 | 154 |
| A422N | TGAGGTTTGATCCG | 1 | 155 |
| A423L | GAGGTTTGATCC | 1 | 156 |
| A424J | AGGTTTGATC | 1 | 157 |
| A425H | GGTTTGAT | 53 | — |
| A426F | GTTTGA | 78 | — |
| A473N | TCACATTTGTTGTG | 3 | 158 |
| A473L | ACATTTGTTGTG | 0 | 159 |
| A473J | ATTTGTTGTG | 1 | 160 |
| A473I | TTTGTTGTG | 49 | — |
| A473H | TTGTTGTG | 33 | — |
| A473F | GTTGTG | 34 | — |
| A497N | GCTCTATCTTTCTT | 1 | 161 |
| A499L | GCTCTATCTTTC | 1 | 162 |
| A501J | GCTCTATCTT | 1 | 163 |
| A503H | GCTCTATC | 1 | — |
| A505F | GCTCTA | 75 | — |
| A513N | ACATTTTTCTTGTC | 0 | 164 |
| A521N | GGCTTGTCACATTT | 1 | 165 |
| A527N | CGCCTCGGCTTGTC | 35 | 166 |

In item "sample #" in Table 1, the nucleotide sequences given "A" before their numbers are antisense chains, i.e. chains complementary to a partial sense chain in the nucleic acid sequence coding for VEGF, and the nucleotide sequences given "S" are sense chains. The nucleotide sequences given "R" are random sequences; for example, the nucleotide sequence "RA101" (SEQ ID NO:93) is identical in nucleotide composition with the nucleotide "A101", (SEQ ID NO:93) but each of its nucleotides is randomly positioned.

The number given for each nucleotide sequence indicates the beginning position of its corresponding nucleotide sequence in SEQ ID NO:1. For example, the nucleotide sequence "A101" (SEQ ID ON:16)is an antisense nucleic acid compound of 20-nucleotides, which consists of a nucleotide sequence complementary to the nucleotide sequence of from the 101- to 120-positions in SEQ ID NO:1. The specific sequence (20 nucleotides) of each sample # is shown in item "nucleotide sequence" in Table 1. The nucleotide sequence "T-20" is a nucleic acid compound consisting of 20 thymidines.

In item "sample #" in Table 2, the designation "A" has the same meaning as in Table 1. Each alphabet after sample number indicates degree of polymerization as follows: F means 6-nucleotides compound; H, 8-nucleotides; I, 9-nucleotides; J, 10-nucleotides; L, 12-nucleotides; N, 14-nucleotides; P, 16-nucleotides; and R, 18-nucleotides. The specific sequence of each sample# is shown in item "nucleotide sequence".

The natural-type and phosphorothioate-type oligodeoxyribonucleotides were examined for their purity with HPLC and UV absorption spectra. The elution conditions, column etc. are as follows:

(I) HPLC (a) For the natural-type oligodeoxyribonucleotide

Sample: A101 (SEQ ID NO:16).

Column: Ion-exchange column (Gen-Pak DNA 6×150 mm available from Waters).

Solvent A: Mixture (9:1) of 25 mm sodium phosphate buffer, pH 6.0 and acetonitrile.

Solvent B: Solvent A plus 1M NaCl.

Figure 2:
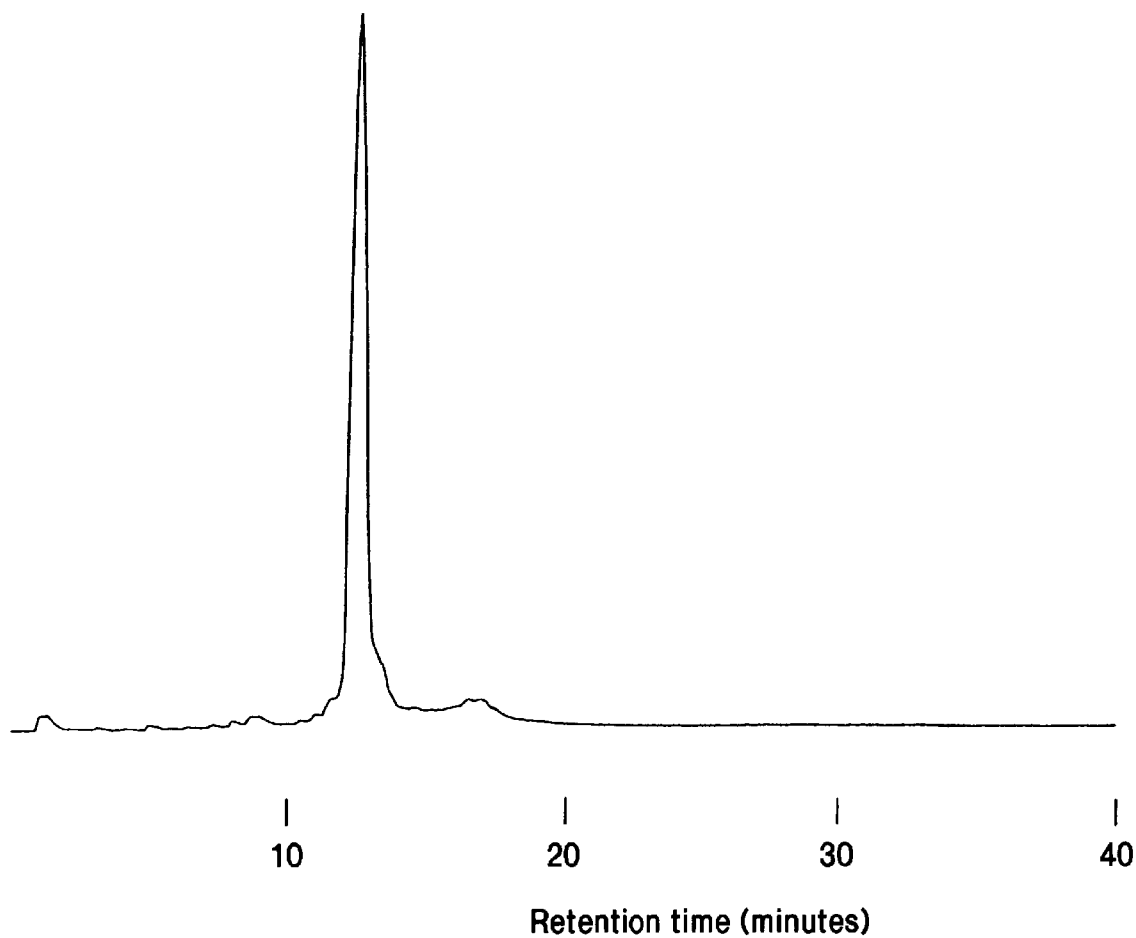
FIG. 2 shows a result of HPLC for a natural-type oligodeoxyribonucleotide.

Elution: Linear gradient at 0.8 ml/min. of from 20% Solvent B (i.e. 80% Solvent A) to 100% Solvent B for 40 min. The result is shown in FIG. 2.

(b) For the phosphorothioate-type oligodeoxyribonucleotide

Sample: Compound S101-S being identical in nucleotide sequence with S101 (SEQ ID NO:92) but having a phosphorothioate-type bond in place of the phosphate diester bond.

Column: Reverse phase column ($\mu$ Bondasphere 5 $\mu$ C18 300 A, 3.9×150 mm, available from Waters).

Solvent A: 0.1M aqueous triethyl ammonium acetate ( pH 7.0).

Solvent B: Acetonitrile.

Elution: Linear gradient at 1 ml/min. of from 10% Solvent B (i.e. 90% Solvent A) to 60% Solvent B for 25 min., and then a constant concentration of 60% Solvent B at 1 ml/min. for 5 min.

Figure 3:
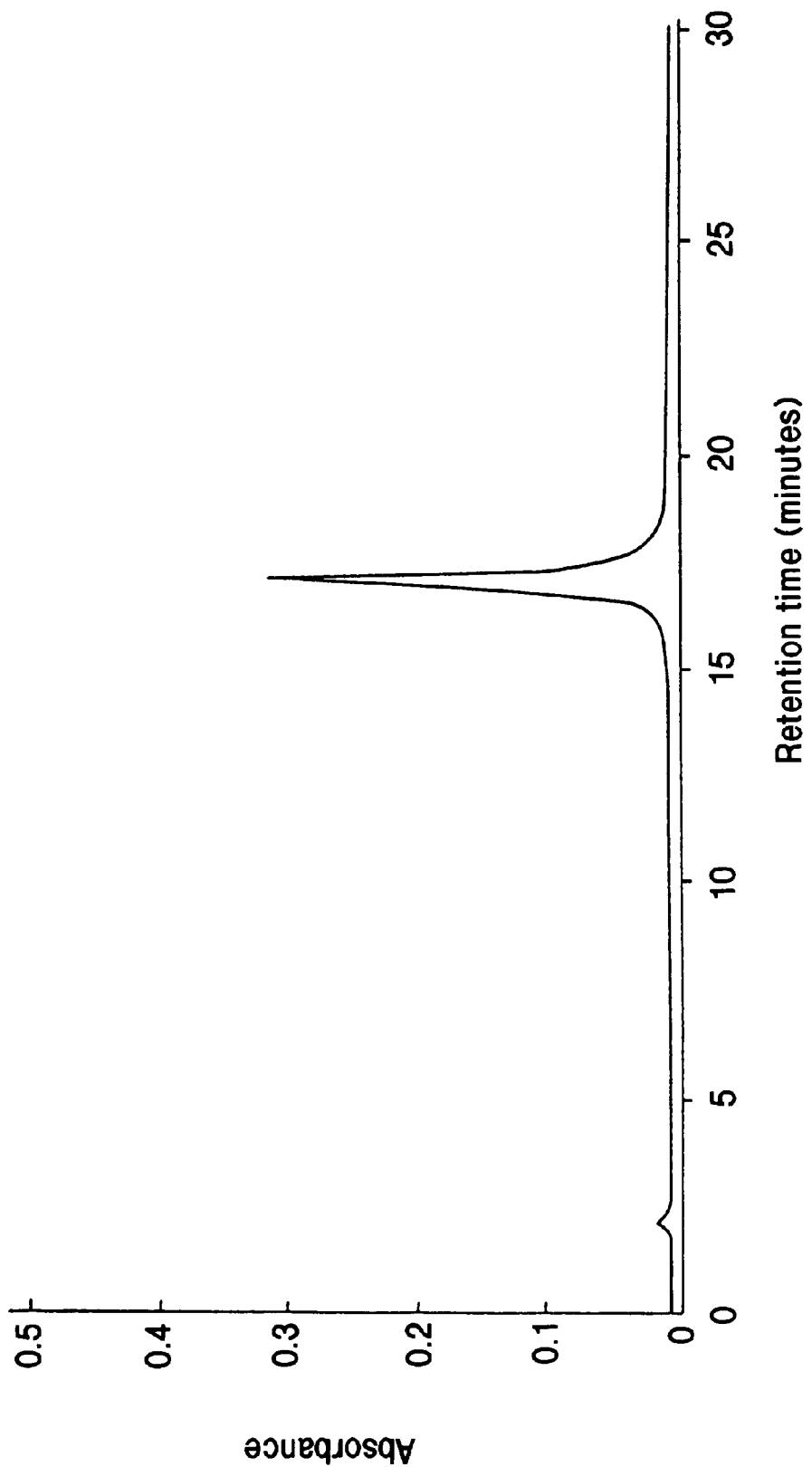
FIG. 3 shows a result of HPLC for a phosphorothioate-type oligodeoxyribonucleotide.

The result is shown in FIG. 3.

(ii) Analysis of UV absorption spectra

Sample: The same natural- and phosphorothioate-type oligodeoxyribonucleotides as used in HPLC.

Solvent: 20 mM sodium phosphate buffer, pH 7.0, plus 0.1M NaCl for both the natural- and phosphorothioate-type oligodeoxyribonucleotides.

Figure 4:
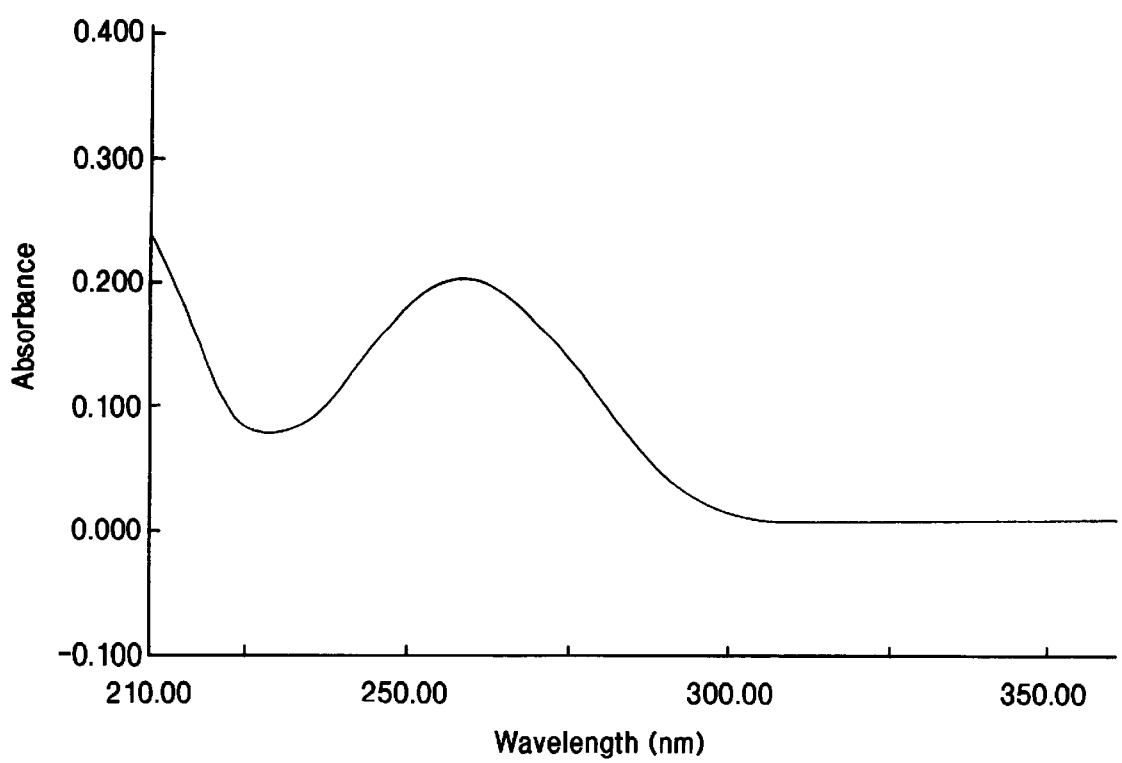
FIG. 4 shows an UV absorption spectrum of a natural-type oligodeoxyribonucleotide.
Figure 5:
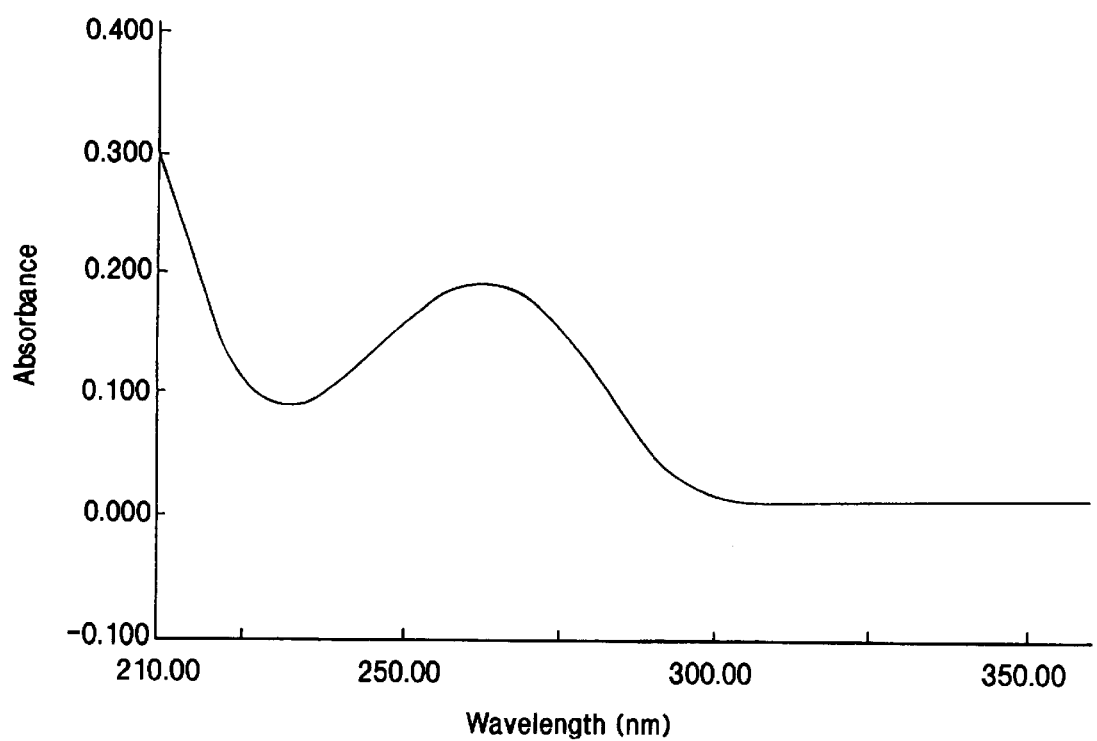
FIG. 5 shows an UV absorption spectrum of a phosphorothioate-type oligodeoxyribonucleotide.

FIGS. 4 and 5 show the results of the natural- and phosphorothioate-type nucleotides, respectively.

FIGS. 2 and 3 show that the purity of these compounds is sufficient for use in the experiments of the present invention. FIGS. 4 and 5 show that the UV absorption spectra of these compounds agree with those of nucleic acid compounds.

(3) Expression of VEGF

A transcription and translation system derived from a rabbit reticulocyte lysate, available from Promega, can be used for expression of VEGF from plasmid pSU02. Because an SP6 promoter is located upstream to the VEGF structural gene in plasmid pSU02, a kit of TNT™ SP6 Coupled Reticulocyte Lysate System was used for transcription and translation of pSU02. The experimental method followed the manufacturer's instructions attached to the kit.

Table 3 shows the composition of the reaction mixture in this transcription and translation system.

TABLE 3

| sample | amount ($\mu$l) |
| --- | --- |
| TNT ™ rabbit reticulocyte lysate | 12.5 |
| TNT ™ reaction buffer | 1.0 |

TABLE 3-continued

| sample | amount ($\mu$l) |
| --- | --- |
| TNT ™ SP6 RNA polymerase | 0.5 |
| Amino acid mixture (1 mM; not containing methionine) | 0.5 |
| $^{35}$S-methionine | 1.0 |
| Ribonuclease Inhibitor (40 U/$\mu$l) | 0.5 |
| pSU02 (0.5 $\mu$g/$\mu$l) | 1.0 |
| Sterilized water | 8.0 |
| Total | 25.0 |

$^{35}$S-methionine was of in vivo cell labeling grade (SJ1015, 37TBq/mmol, 0.37 MBq $\mu$l) manufactured by Amersham and it was added in a half (1 $\mu$l) of the prescribed amount in the instructions attached to the kit of Promega. The ribonuclease inhibitor was supplied from Takara Shuzo Co., Ltd., and the sterilized water was previously treated at 121° C. for 15 minutes. The other ingredients except for pSU02 were those contained in the kit of Promega. The above reaction mixture was incubated at 30° C. or 37° C. for 1 to 2 hours to produce 10 to 100 ng of the protein of VEGF.

(4) Confirmation of expression of VEGF (i) Enzyme immunoassays

Anti-VEGF polyclonal antibodies obtained from a rabbit given human-derived VEGF produced by E. coli were immobilized in a usual manner onto a polystyrene microtiter plate. Then, the mixture described in (3) above (previously reacted at 30° C. for 2 hours) for the transcription and translation system for VEGF was diluted 3- to 9375-fold and the diluted mixture was added to each well. The plate was left at room temperature (25° C.) for 2 hours. The diluted mixture was removed, and the plate was washed with a phosphate buffer containing 0.1% bovine serum albumin. Then, other anti-VEGF polyclonal antibodies labeled with horseradish peroxidase were added to each well and left at room temperature for 1 hour. The plate was washed sufficiently with the same phosphate buffer, and an ortho-diaminobenzene solution was added thereto as substrate and left at room temperature until suitable coloration took place (about 30 minutes). Thereafter, the absorbance of each solution was determined at 490 nm to evaluate its VEGF content.

Figure 6:
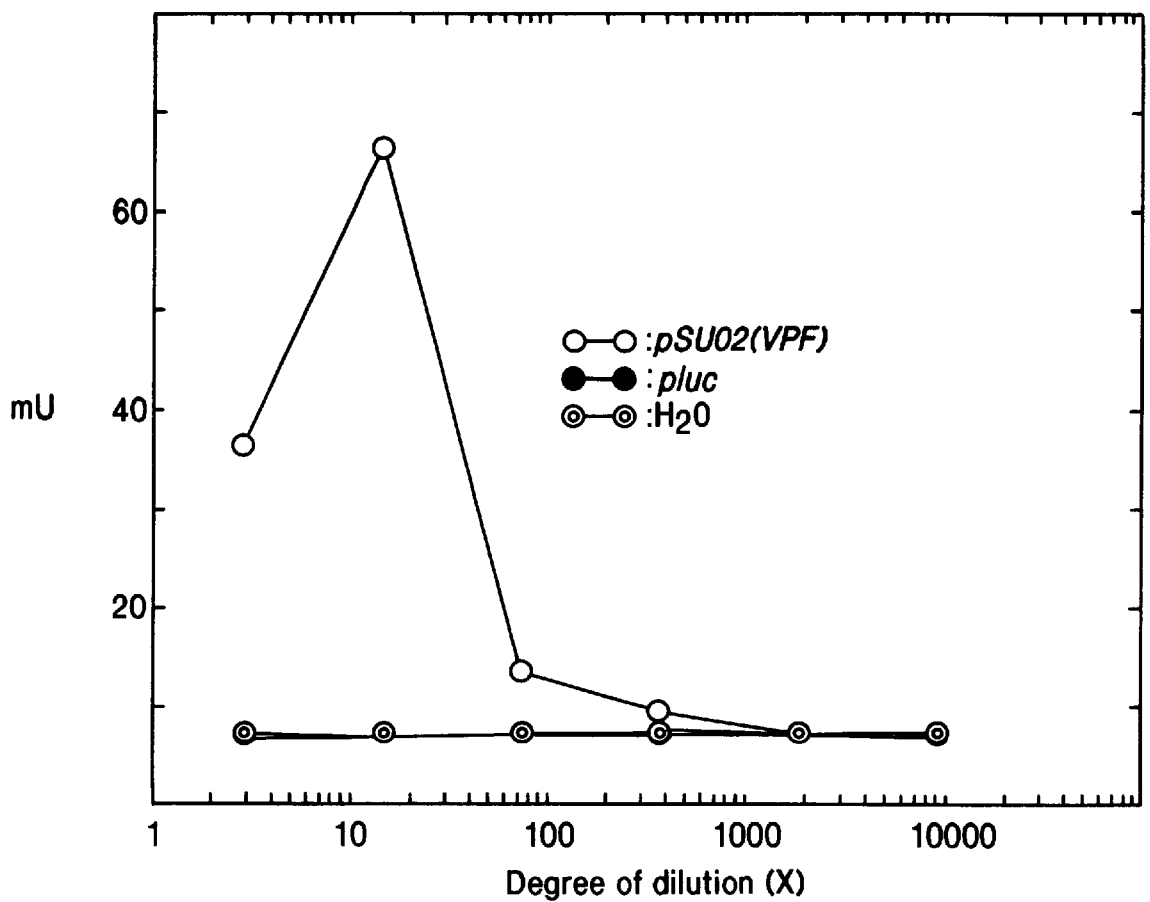
FIG. 6 shows the amount of VEGF expressed as determined by enzyme immunoassays.

The results are shown in FIG. 6. If pSU02 was used as the plasmid, the absorbance of the protein (VEGF) ("○" in the graph) was evidently higher in low degree of dilution (from 3-fold to 375-fold) than in high degree of dilution (from 1875-fold to 9375-fold) of the reaction mixture. On the other hand, if pPoly(A)-luc(SP6) not producing VEGF was used as the plasmid, the absorbance remained nearly constant ("●" in the graph and overlapped with ⊙).

That is, if pPoly(A)-luc(SP6) was used as the plasmid, the absorbance is substantially the same as in high degree of dilution of the reaction mixture as well as in the control ("⊙" in the graph) where water was used in place of pSu02.

Hence, it can be concluded that the higher absorbance in the case of low dilution of the pSU02-containing reaction mixture was due to the production of VEGF in the transcription and translation system. Three-fold dilution of the reaction mixture containing pSU02 as the plasmid gave lower absorbance than 15-fold dilution of the same reaction mixture. This suggests that the reaction mixture contained a substance significantly inhibiting the reaction between VEGF and the polyclonal antibodies.

(ii) Electrophoresis

The formation of VEGF in the above transcription and translation system was confirmed in SDS-PAGE (sodium dodecyl sulfate-polyacrylamide gel electrophoresis).

SDS-PAGE was carried out in the following manner according to the instructions attached to the transcription and translation system kit available from Promega.

Five μl of the reaction mixture in the transcription and translation system was added to 20 μl of 2-mercaptoethanol containing SDS sample buffer with the composition in accordance with the instructions of Promega. The mixture was sealed and heated at 100° C. for 2 minutes to denature the protein. Five μl of the mixture was removed and electrophoresed by SDS-PAGE (15% or 17.5% polyacrylamide gel). For autoradiography, the gel was transferred to a filter paper and dried sufficiently at 80° C. in an oven. Then, the gel was laid on X-ray film in the dark to be introduced into a cassette. This cassette was left at room temperature for 10 to 100 hours, and the X-ray film was developed.

Figure 7:
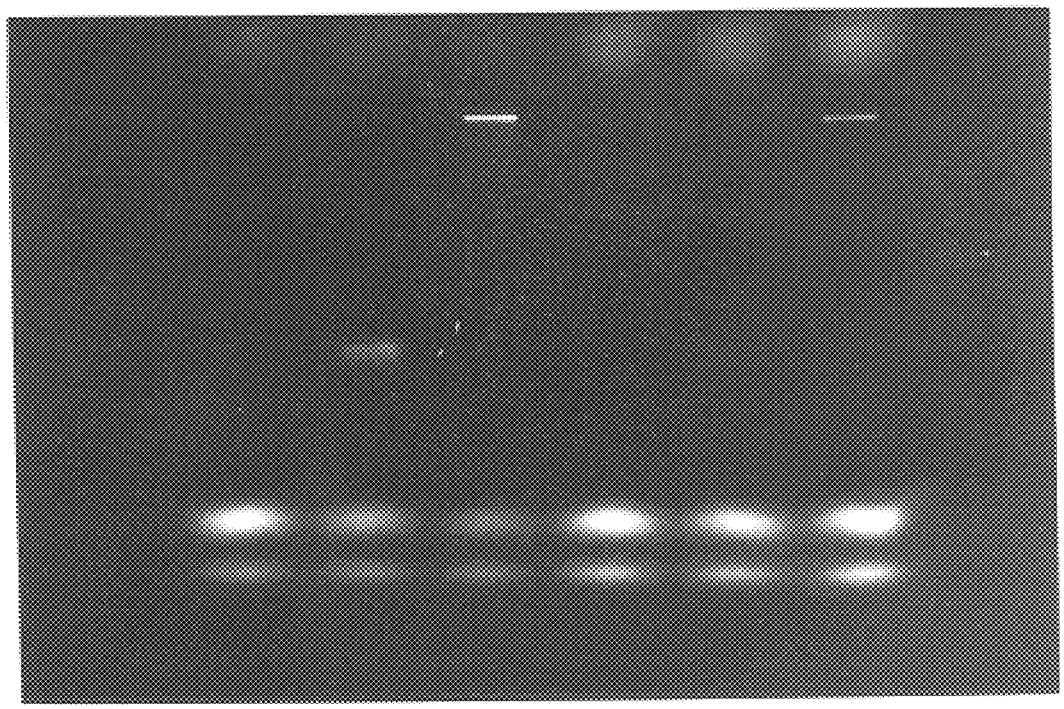
FIG. 7 shows results of SDS-PAGE for VEGF and luciferase formed in a transcription and translation system. Lanes 1 and 3 show a band of VEGF expressed using plasmid pSU02, and lanes 2 and 4 show a band of luciferase expressed using plasmid pPoly(A)-luc(SP6).

The result is shown in FIG. 7. Lanes 1 and 3 show bands of the reaction mixture where pSU02 was used as the plasmid, and lanes 2 and 4 show bands of the reaction mixture where pPoly(A)-luc(SP6) was used as the plasmid. The reaction mixtures used in lanes 1 and 2 were previously incubated at 30° C. for 2 hours in the transcription and translation system, while the reaction mixtures in lanes 3 and 4 were previously incubated at 37° C. for 2 hours in the system. The molecular weight of each band was estimated from the positions of simultaneously electrophoresed pigment-labeled proteins as the molecular-weight marker [Rainbow™ marker (high-molecular range)]. If pSU02 was used as the plasmid, a band with a molecular weight of about 15 kd was observed, but if pPoly(A)-luc(SP6) was used as the plasmid, a band appeared at a molecular weight of about 60 kd in place of said band of about 15 kd. The molecular weight of VEGF produced using plasmid pSU02 estimated to be 17.2 kd from its amino acid sequence, and from this molecular weight it is understood that VEGF was produced from plasmid pSU02.

(5) Screening

On the basis of the results of (1) to (4) above, screening was carried out using the transcription and translation system (Promega) derived from a rabbit reticulocyte lysate.

First, the optimum conditions for screening were examined in the following manner.

(i) Examination of natural-type and phosphorothioate-type oligodeoxyribonucleotides and reaction temperature Whether the oligodeoxyribonucleotides (natural-type and phosphorothioate-type) obtained in (2) above are suitable for use in screening as the antisense nucleic acid compound was evaluated by examining their stability and effect on the transcription and translation system. The results are shown below.

The natural-type and phosphorothioate-type oligodeoxyribonucleotides each consisting of about 20 nucleotides were labeled at the 5'-terminal with a $^{32}$P-phosphate group by use of T4 polynucleotide kinase (Takara Shuzo Co., Ltd.), and their stability was examined in the transcription and translation system (Promega) derived from a rabbit reticulocyte lysate. The result indicated that almost all the natural-type and phosphorothioate-type oligodeoxyribonucleotides remained stable at 30° C. for 3 hours or at 37° C. for 2.5 hours. The decomposition of the natural-type and phosphorothioate-type oligodeoxyribonucleotides, particularly at 37° C. for 1 hour, was almost negligible.

From this result, it can be concluded that the natural-type and phosphorothioate-type oligodeoxyribonucleotides are suitable for use in screening to examine the effect of antisense nucleic acid compound. Although it was found that the screening temperature in the transcription and translation system (Promega) derived from a rabbit reticulocyte lysate may be 30° C. and 37° C., the latter was adopted for screening since 37° C. is near the body temperature.

(ii) Examination of the action of RNase H

The effect of RNase H (enzyme cleaving a double-stranded chain of a hybrid between mRNA and the antisense nucleic acid compound) on the transcription and translation system (Promega) used in screening of the antisense nucleic acid compound was examined by SDS-PAGE and autoradiography. The reaction mixture in the transcription and translation system for this purpose is shown in Table 4.

TABLE 4

| sample | amount (μl) |
| --- | --- |
| TNT ™ rabbit reticulocyte lysate | 5.0 |
| TNT ™ reaction buffer | 0.4 |
| TNT ™ SP6 RNA polymerase | 0.2 |
| Amino acid mixture (1 mM; not containing methionine) | 0.2 |
| $^{35}$S-methionine | 0.8 |
| Ribonuclease Inhibitor (40 U/μl) | 0.2 |
| Plasmid PSU02 (0.5 μg/μl) | 0.4 |
| RNase H or sterilized water | 2.8 |
| Total | 10.0 |

In the above composition, the ingredients other than RNase H were those described in (1) or (3) above. RNase H, available from Takara Shuzo Co., Ltd., was adjusted to 1, 5, or 25 U in total in the reaction mixture. After incubation at 37° C. for 1 hour, the reaction mixture was subjected to SDS-PAGE and autoradiography as described in (4) above. The result is shown in FIG. 8.

This result indicated that the addition of RNase H brought about no significant decrease in the density of the VEGF band ("→" in FIG. 8), and thus it was confirmed that the activity of the transcription and translation system (Promega) was not decreased even by addition of RNase H.

Figure 8:
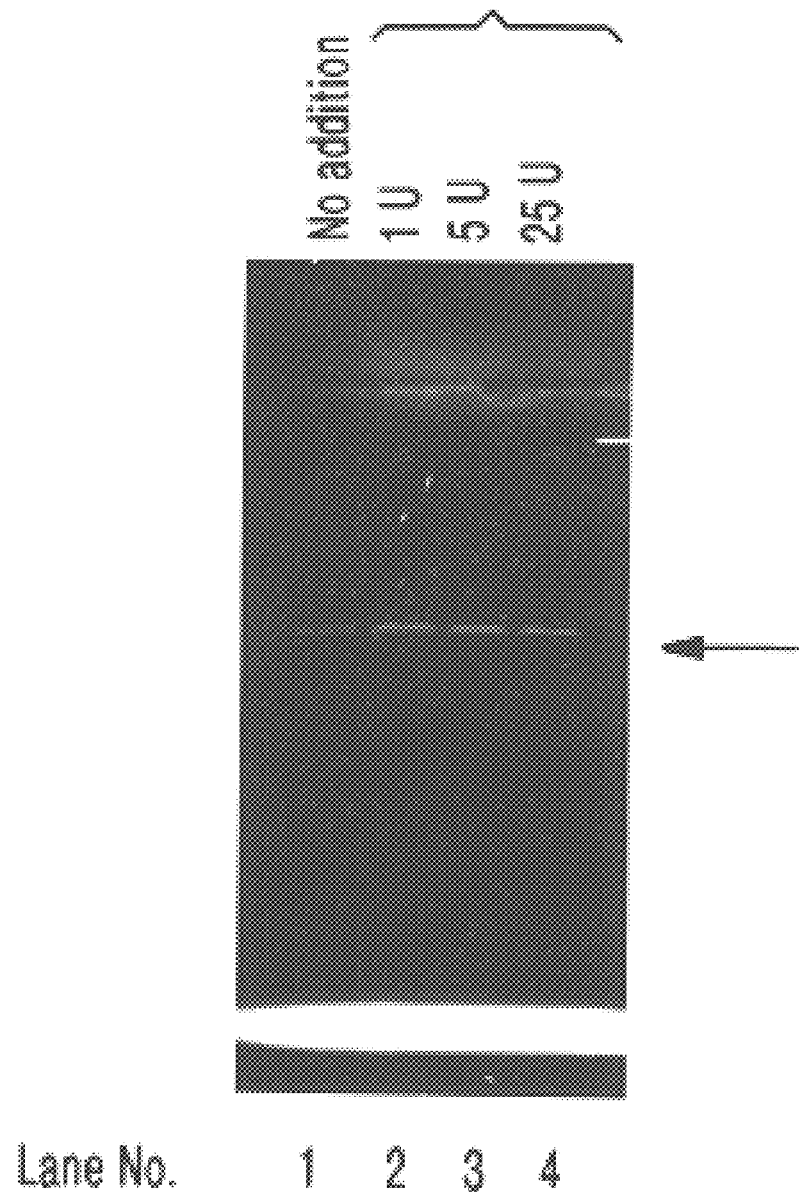
FIG. 8 shows SDS-PAGE analysis for the effect of RNase H on the activity of a transcription and translation system derived from rabbit reticulocyte lysate (lane 1 in the absence of RNase H, and lanes 2, 3 and 4 in the presence of 1, 5 and 25 U RNase H, respectively).

In FIG. 8, lane 1 shows the reaction mixture where RNase H was not added, and lanes 2, 3 and 4 show the reaction mixtures containing 1, 5, and 25 U RNase H, respectively.

It was then examined whether RNaseH activity can appear in the transcription and translation system (Promega) derived from a rabbit reticulocyte lysate. This examination was carried out in the following manner by referring to the method of the literature (I. Berkower et al., Journal of Biological Chemistry, vol. 248, pp. 5914–5921 (1974)). The composition of the assay mixture is shown in Table 5.

TABLE 5

| sample | amount (μl) |
| --- | --- |
| TNT ™ rabbit reticulocyte lysate | 12.5 |
| TNT ™ reaction buffer | 1.0 |
| TNT ™ SP6 RNA polymerase | 0.5 |
| Amino acid mixture (1 mM; not containing 1 mM methionine) | 0.5 |
| Amino acid mixture (1 mM; not containinq 1 mM leucine) | 0.5 |
| Ribonuclease Inhibitor (40 U/μl) | 0.5 |
| Plasmid pSU02 (0.5 μg/μl) | 1.0 |
| poly[$^3$H-rA] (0.1 μg/μl) | 1.1 |
| poly[dT] (0.1 μg/μl) | 1.0 |
| RNase H (1.0 or 10.0 U/μl) | 1.0 (or 2.5) |
| Sterilized water | 5.4 (or 3.9) |
| Total | 25.0 |

The ingredient poly[$^3$H-rA], available from Amersham, had a polymerization degree of 38 to 137 and a radioactivity of 51.8 MBq/mg. The ingredient poly[dT] available from Pharmacia had a mean polymerization degree of 174. The amino acid mixture (1 mM, not containing leucine) was contained in the transcription and translation system (Promega) derived from a rabbit reticulocyte lysate. The other ingredients were those described in (1) or (3) above.

The above mixture was incubated at 37° C. for 20 minutes, and then the following regents were added.

| | |
|---|---|
| 0.1 M sodium pyrophosphate (4° C.) | 50 µl |
| Salmon sperm DNA (thermally denatured, 1 mg/ml) | 25 µl |
| Bovine serum albumin (10 mg/ml) | 50 µl |
| 10% aqueous trichloroacetic acid | 150 µl |

Figure 9:
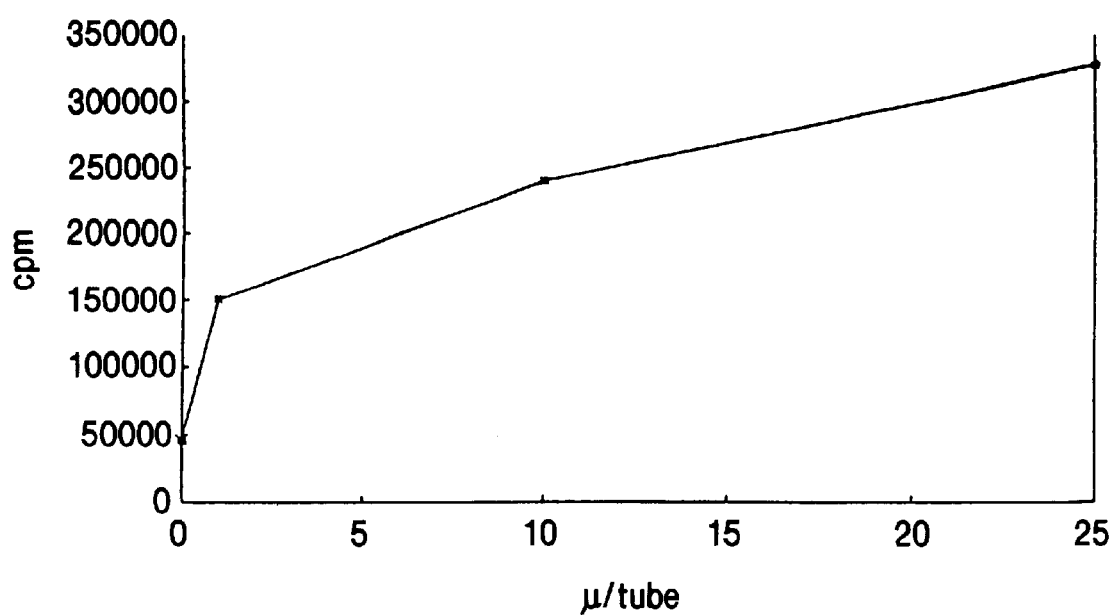
FIG. 9 shows activity of RNase H in a transcription and translation system.

The mixture thus obtained was gently stirred and then centrifuged at 4000 r.p.m. for 2 minutes. The supernatant was introduced into a minivial for liquid scintillation, and 2 ml reagent for liquid scintillation (Ultima Gold, manufactured by Packard) was introduced into the minivial. The mixture was gently shaken and examined for radioactivity in a liquid scintillation counter (Beckman). The result indicated that the significant activity of RNase H was present under the conditions of the above reaction (FIG. 9).

The influence of coexistent RNase H on the effect of the oligodeoxyribonucleotide in different concentrations was examined. The experimental method is as follows:

The amount of VEGF expressed in the presence or absence of RNase H, with the nucleic acid compound in a concentration ranging from 0 to 2000 nM, was determined as described above in (4) (ii). For this experiment, RNase H (11.4 U) and the nucleic acid compound (final concentration: 16 to 2000 nM) were added as necessary to the reaction mixture shown in Table 3.

Figure 10:
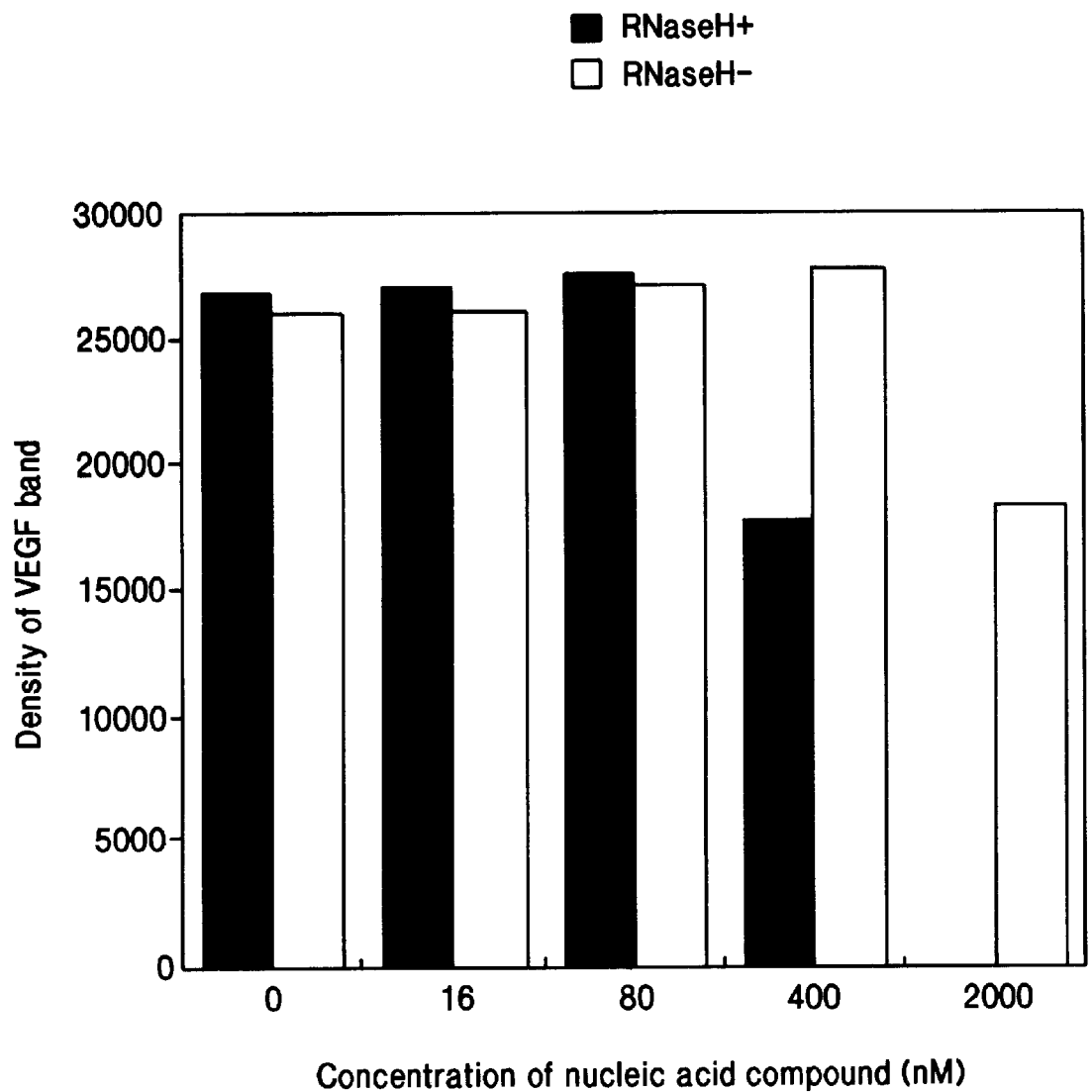
FIG. 10 shows the effect of the nucleic acid compound on the expression of VEGF ("■" in the presence of RNase H and "□" in the absence of RNase H).
Figure 11:
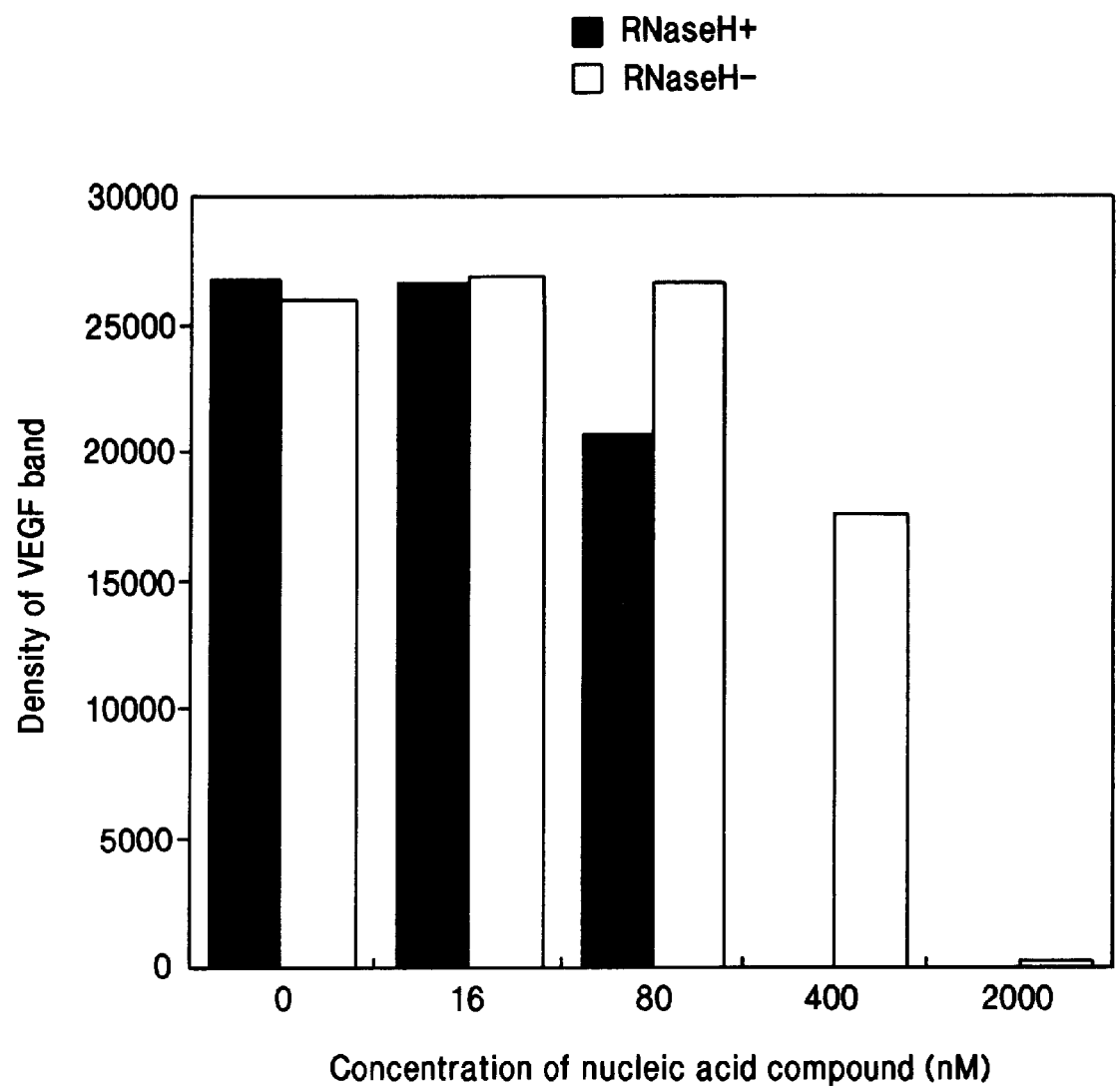
FIG. 11 shows the effect of the nucleic acid compound on the expression of VEGF ("■" in the presence of RNase H and "□" in the absence of RNase H).

The results are shown in FIGS. 10 and 11. FIGS. 10 and 11 show bands of the reaction mixtures where A101 (SEQ ID NO:16) and A143 (SEQ ID NO:23) were used as the nucleic acid compounds, respectively. In this graph, the concentration (nM) of the nucleic acid compound is indicated on the abscissa, and density in autoradiography determined by a densitometer (i.e. the amount of expressed VEGF) on the ordinate, with "■" in the presence of RNase H and "□" in the absence of RNase H.

As can be seen from these graphs, the inhibitory effect of the oligodeoxyribonucleotide (antisense nucleic acid compound) on the expression of VEGF was reinforced by the coexistent RNase H. That is, the expression of VEGF could be inhibited by the oligodeoxyribonucleotide in lower concentration.

From these results, RNase H was adopted for screening of the desired antisense nucleic acid compound.

(iii) Examination of concentration of nucleic acid compound

The optimum nucleic acid concentration was examined for screening of the desired antisense nucleic acid compound. The experimental method is as follows:

The amount of VEGF expressed in the presence or absence of RNase H with the nucleic acid compound in a concentration ranging from 0 to 2000 nM was determined as described above in (4) (ii). For this experiment, RNase H (11.4 U) and the nucleic acid compound (final concentration: 16 to 2000 nM) were added additionally to the reaction mixture shown in Table 3.

Figure 12:
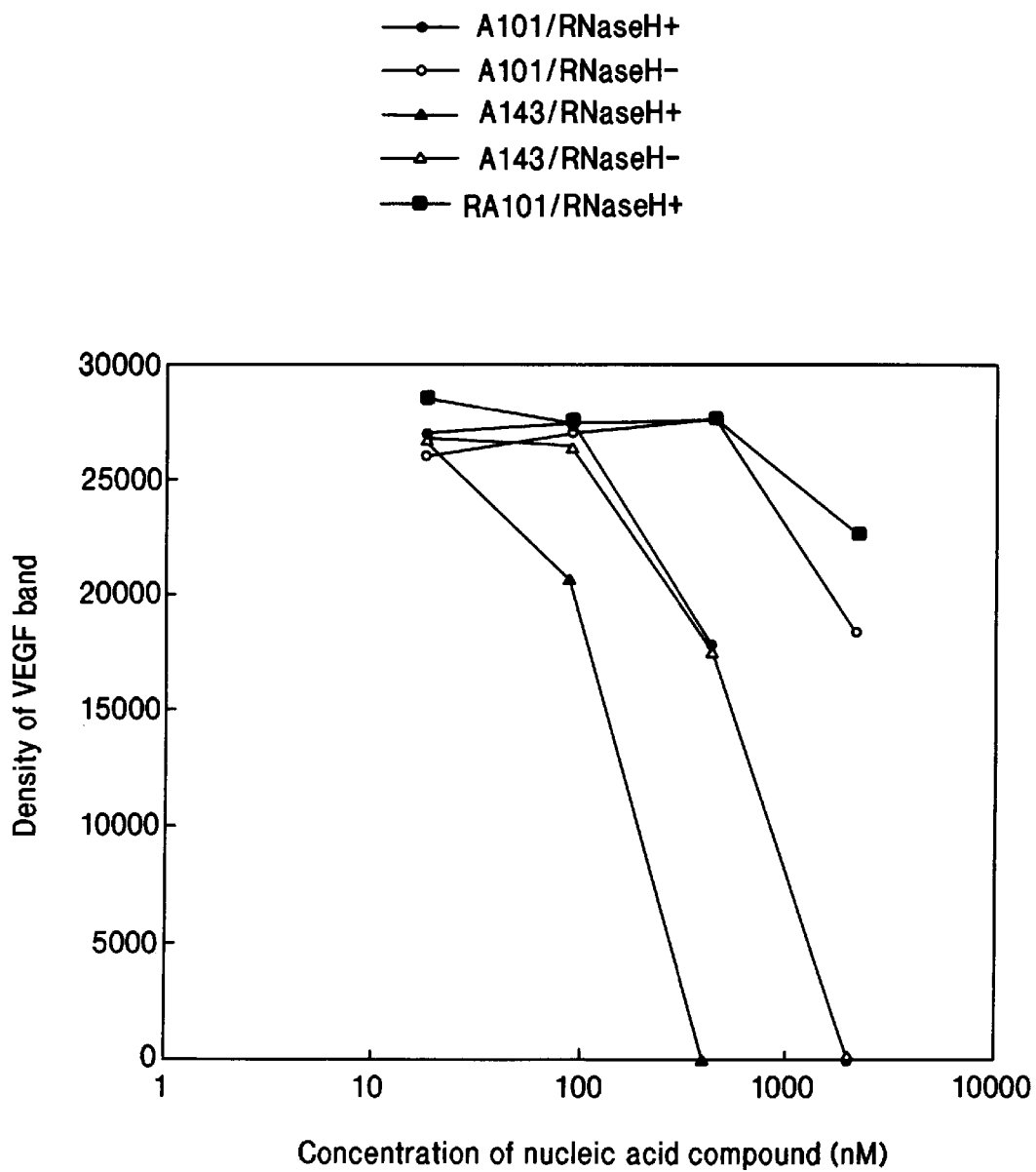
FIG. 12 shows the effect of the nucleic acid compound on the expression of VEGF ("—●—" with the nucleic acid compound A101 (SEQ ID NO:16) in the presence of 11.4 U RNase H, "—○—" with A101 (SEQ ID NO:16) in the absence of RNase H, "—▲—" with A143 (SEQ ID NO:23) in the presence of 11.4 U RNase H, "—△—" with A143 (SEQ ID NO:23) in the absence of RNase H, and "—■—" with RA101 (SEQ ID NO:93) in the presence of 11.4 U RNase H).

The result is shown in FIG. 12. In this graph, "—●—" indicates the amount of VEGF expressed with A101 (SEQ ID NO:16) as the nucleic acid compound in the presence of 11.4 U RNase H (indicated as "RNase H+"); "—○—", with A101 (SEQ ID NO:16) in the absence of RNase H (indicated as "RNase H−"); "—▲—", with A143 (SEQ ID NO:23) in the presence of 11.4 U RNase H; "—△—", with A143 (SEQ ID NO:23) in absence of RNase H; and "—■—", with RA101 (SEQ ID NO:93) in the presence of 11.4 U RNase H.

Because the inhibitory effect of 0.08 µM or less nucleic acid compound on the expression of VEGF was not significant, 0.4 µM nucleic acid compound was adopted for screening, because with this concentration, the inhibitory effect on the expression of VEGF clearly appeared depending on the type of oligodeoxyribonucleotide.

From the results in (i) to (iii) above, screening was carried out.

The composition of the assay mixture per tube is shown in Table 6.

TABLE 6

| sample | amount (µl) |
|---|---|
| TNT ™ rabbit reticulocyte lysate | 12.5 |
| TNT ™ reaction buffer | 1.0 |
| TNT ™ SP6 RNA polymerase | 0.5 |
| Amino acid mixture (1 mM; not containing 1 mM methionine) | 0.5 |
| Ribonuclease Inhibitor (40 U/µl) | 0.5 |
| RNase H (60 U/µl) | 0.19 |
| $^{35}$S-methionine | 1.0 |
| Plasmid pSU02 (0.5 µg/µl) | 1.0 |
| Nucleic acid compound (5 µM) | 2.0 |
| Sterilized water | 5.81 |
| Total | 25.0 |

The composition was prepared as described above. The sample was incubated at 37° C. for 1 hour. Then, the amount of expressed VEGF was examined by SDS-PAGE and autoradiography as described above in (4) (ii). After autoradiography, the density was measured with a densitometer (Bio-Profil 1-D, M&S Instruments Trading, Inc.) and then compared with a standard curve to evaluate the expression of VEGF as follows:

The produced VEGF was separated by SDS-PAGE and then subjected to autoradiography, and the density was determined. The produced VEGF was estimated by comparing this density with that of a standard curve prepared using the same composition as above but not containing the antisense nucleic acid compound. The result was indicated as a relative value to the amount (as 100%) of VEGF expressed in the absence of the antisense nucleic acid compound.

To confirm reproducibility, 2 samples were prepared for each compound in the above composition, and the amount of VEGF produced in each sample was determined where 2 lanes were used for each sample.

As a result, the relative error of expression (%) was usually about 10% or less and maximally about 30%.

Table 1 shows the effect of each oligodeoxyribonucleotide consisting of 20 nucleotides and Table 2 shows the effect of each oligodeoxyribonucleotide consisting of other than 20 nucleotides in screening for a desired antisense nucleic acid compound. In Tables 1 and 2, a less value in item "expression (%)" means a higher inhibitory effect of the test compound on the expression of the VEGF gene.

Tables 1 and 2 evidently indicate the presence of oligodeoxyribonucleotides inhibiting the expression of VEGF. Among these, there are (1) oligodeoxyribonucleotides having an extremely strong inhibitory effect on the expression of VEGF (inhibiting the amount of expressed VEGF to a level of 10% or less) and (2) oligodeoxyribonucleotides having a strong inhibitory effect on the expression of VEGF (inhibiting the amount of expressed VEGF to a level of 30% or less).

As can be seen from Table 1, all 24 oligodeoxyribonucleotides from A383 (SEQ ID NO:63) to A521 (SEQ ID NO:86), 6-nucleotides apart from each other, have an extremely strong inhibitory effect (10% or less expression). That is, antisense nucleic acid compounds towards some regions within the 383-position or thereabout to the 521-position or thereabout in SEQ ID NO:1 have an extremely strong inhibitory effect (10% or less expression) on the production of VEGF (said region is hereinafter referred to as "core region".).

The effect of antisense nucleic acid compounds towards partial nucleotide sequences in the core region was examined using different chain lengths.

The nucleotide sequences shown in A422N (SEQ ID NO155) to A426F, A473N (SEQ ID NO:158) to A473F, and A497N (SEQ ID NO:161) to A505F in Table 2 were examined for their inhibitory effect on the expression of the VEGF gene.

As a result, a chain length of not less than 10 nucleotides gave an extremely strong inhibitory effect (10% or less expression); the chain length of 6 nucleotides gave no or little inhibitory effect; the chain length of 8 nucleotides gave no effect (1 case), little effect (1 case), or a strong effect (1 case). This different effect of the chain length of 8 nucleotides may be attributable to the difference in the nucleotide sequence or nucleotide composition.

From the results, it is expected that an antisense nucleic acid compound complementary to 10 nucleotides in the core region generally has a strong inhibitory effect on the expression of the target protein (VEGF) and also that an antisense nucleic acid compound complementary to about 8 nucleotides within the core region possibly has a strong inhibitory effect on the expression of the target protein.

From these results and this expectation, it can be estimated that the core regions within the 77- to 570-positions in SEQ NO: 1 are the nucleotide sequences of from the 95- to 108-positions (SEQ ID NO:2), 149- to 174-positions (SEQ ID NO:3), 185- to 210-positions (SEQ ID NO:4), 219- to 244-positions (SEQ ID NO:5), 254- to 276-positions (SEQ ID NO:6), 287- to 328-positions (SEQ ID NO:7), 357- to 372-positions (SEQ ID NO:8), and 389- to 534-positions (SEQ ID NO:9). The core regions are preferably those of SEQ ID NOS:2, 4 and 5, more preferably SEQ ID NOS:6, 7 and 9. An antisense nucleic acid compound complementary to 8 nucleotides, preferably contiguous 8 or more nucleotides, within these core regions shows a significant inhibitory effect on the expression of VEGF, as can be seen from Tables 1 and 2. As the antisense nucleic acid compound complementary to 8 nucleotides in the core regions, mention may be made of antisense nucleic acid compounds A085R (SEQ ID NO:99), A087P (SEQ ID NO:100), A089N (SEQ ID NO:101), A101N (SEQ ID NO:103), A167N (SEQ ID NO:114), A179N (SEQ ID NO:117), A203N (SEQ ID NO:121), A213N (SEQ ID NO:123), A237N (SEQ ID NO:125), A248N (SEQ ID NO:128), A321N (SEQ ID NO;141), A365N (SEQ ID NO:148), and A383N (SEQ ID NO:153). As the antisense nucleic acid compound complementary to 9 or more nucleotides in the core regions, mention may be made of A089 (SEQ ID NO:14), A095 (SEQ ID NO:15), A095N (SEQ ID NO:102), A143 (SEQ ID NO:23), A146N (SEQ ID NO:109), A149 (SEQ ID NO:24), A153N (SEQ ID NO:110), A155 (SEQ ID NO:25), A155N (SEQ ID NO:111), A156N (SEQ ID NO:112), A161 (SEQ ID NO:26), A179 (SEQ ID NO:29), A185 (SEQ ID NO:30), A189N (SEQ ID NO:118, A191 (SEQ ID NO:31), A191N (SEQ ID NO:119), A193N (SEQ ID NO:120), A197 (SEQ ID NO:32), A217N (SEQ ID NO:124), A227 (SEQ ID NO:37), A251 (SEQ ID NO:41), A251N (SEQ ID NO:129), A257 (SEQ ID NO:42), A261N (SEQ ID NO:130), A263 (SEQ ID NO:43, A263N (SEQ ID NO:131), A265N (SEQ ID NO:132), A281 (SEQ ID NO:46), A287 (SEQ ID NO:47), A293N (SEQ ID NO:134), A296N (SEQ ID NO:135), A299 (SEQ ID NO:49, A299N (SEQ ID NO:136), A303N (SEQ ID NO:137), A305 (SEQ ID NO:50), A311 (SEQ ID NO:51), A313N (SEQ ID NO:138), A317N (SEQ ID NO:139), A347 (SEQ ID NO:57), A353 (SEQ ID NO:58), A356N (SEQ ID NO:146), A359 (SEQ ID NO:59), A361N (SEQ ID NO:147), A397N (SEQ ID NO:154), A513N (SEQ ID NO:164), A521N (SEQ ID NO:165), and 24 antisense nucleic acid compounds of A383 to A521 (SEQ ID NO:63 through 86, respectively) in Table 1.

Then, the antisense nucleic acid compounds being complementary to nucleotide sequences in the core regions but containing a mismatched nucleotide were examined. As opposed to the known correct base pairs (GC, AT and AU), mismatched base pairs are an AA base pair, AG base pair, AC base pair, GG base pair, GT base pair, GU base pair, CC base pair, CT base pair, CU base pair, TT base pair, TU base pair, and UU base pair. Antisense nucleic acid compounds containing a mismatched nucleotide towards T at the 117-position in SEQ ID NO:9 were synthesized and examined for their inhibitory effect on the expression of VEGF. Table 7 shows antisense compounds each containing one mismatched nucleotide (sample#), their nucleotide sequences and their inhibitory effect on the expression of VEGF (%) as well as on the expression of luciferase as the control. The expression of VEGF (%) was determined by use of the composition shown in Table 6 and expressed as a relative value to the value (100%) of the composition in the absence of the nucleic acid compound. The expression of luciferase was determined using plasmid pPoly(A)-Luc(SP6) as the control containing the luciferase gene in place of the VEGF structural gene, and is expressed as a relative value to the value (100%) in the absence of the nucleic acid compound. In item "sample #" in Table 7, the sample given "M" contains a mismatched nucleotide, and the sample given "A" before its number is a antisense chain i.e. a chain complementary to a partial sense chain in the VEGF gene. The number given after "A" indicates the beginning position of its corresponding nucleotide sequence in SEQ ID NO:1. The alphabet given after this number indicates degree of polymerization as follows: L means 12-nucleotides compound; I, 9-nucleotides; K, 11-nucleotides; M, 13-nucleotides; and N, 14-nucleotides. The first number in the parentheses is the number of contiguous complementary nucleotides in the 3'-side, and the latter number is the number of complementary nucleotides in the 5'-side. The alphabet "G" between the numbers in the parentheses is a mismatched nucleotide in the antisense nucleic acid compound. Mismatched nucleotides are underlined in the nucleotide sequences in Table 7. In item "expression of VEGF (%)", the value in the parentheses indicates expression of VEGF (%) in the presence of 50 µM nucleic acid compound (in the case of *1) and 250 µM (in the case of *2) in place of 5 µM in the composition shown in Table 6, and in these cases, the final concentrations of the nucleic acid compound in each reaction solution correspond to 4 µM, and 20 µM, respectively.

TABLE 7

| sample # | nucleotide sequence 5'← →3' | expression of VEGF (%) | expression of luciferase (%) | SEQ. ID NO. |
|---|---|---|---|---|
| MA489L(7G4) | CTCTGTGTTTCT | 4 | — | 167 |
| MA489L(7C4) | CTCTCTGTTTCT | 53 | — | 168 |
| MA501L(4G7) | TTGCTCTGTCTT | 0 | 88 | 169 |
| MA501L(4C7) | TTGCTCTCTCTT | 0 | 72 | 170 |
| MA499L(6G5) | GCTCTGTCTTTC | 6 | 88 | 171 |
| MA499L(6C5) | GCTCTCTCTTTC | 1 | 50 | 172 |
| MA500L(5G6) | TGCTCTGTCTTT | 7 | 76 | 173 |
| MA500L(5C6) | TGCTCTCTCTTT | 16 | 62 | 174 |
| MA498M(7G5) | GCTCTGTCTTTCT | 1 | 60 | 175 |
| MA498M(7C5) | GCTCTCTCTTTCT | 1 | 45 | 176 |
| MA500M(5G7) | TTGCTCTGTCTTT | 0 | 78 | 177 |
| MA500M(5C7) | TTGCTCTCTCTTT | 0 | 75 | 178 |
| MA499M(6G6) | TGCTCTGTCTTTC | 0 | 71 | 179 |
| MA499M(6C6) | TGCTCTCTCTTTC | 4 | 53 | 180 |
| MA498N(7G6) | TGCTCTGTCTTTCT | 1 | 45 | 181 |
| MA498N(7C6) | TGCTCTCTCTTTCT | 4 | 41 | 182 |
| MA499N(6G7) | TTGCTCTGTCTTTC | 0 | 71 | 183 |
| MA499N(6C7) | TTGCTCTCTCTTTC | 0 | 19 | 184 |
| MA502K(5C5) | GCTCTCTCTTT | (0) *1 | — | 185 |
| MA501I(4C4) | CTCTCTCTT | (0) *2 | — | — |

Based on the results of Table 7, for antisense nucleic acid compounds complementary to core regions with one mismatched nucleotide, those antisense compounds having contiguous at least 5 complementary nucleotides as a shorter sequence interrupted by said mismatched nucleotide and having at the same time at least 11 complementary nucleotides in total (at least 12 nucleotides including one mismatched nucleotide) show the same or almost the same inhibitory effect as antisense compounds complementary to contiguous at least 8 to 10 nucleotides. Such antisense nucleic acid compounds containing one mismatched nucleotide include MA499L(6G5) (SEQ ID NO:171), MA499L(6C5) (SEQ ID NO:172), MA500L(5G6) (SEQ ID NO:173), MA500L(5C6) (SEQ ID NO:174), MA498M(7G5) (SEQ ID NO:175), MA498M(7C5) (SEQ ID NO:176), MA500M(5G7) (SEQ ID NO:177), MA500M(5C7) (SEQ ID NO:178), MA499M(6G6) (SEQ ID NO:179), MA499M(6C6) (SEQ ID NO:180), MA498N(7G6) (SEQ ID NO:181), MA498N(7C6) (SEQ ID NO:182), MA499N(6G7) (SEQ ID NO:183), and MA499N(6C7) (SEQ ID NO:184). The expression of VEGF can be inhibited by an antisense nucleic acid compound of 11 nucleotides containing one mismatched nucleotide (i.e. with 10 complementary nucleotides) if used at a final concentration of 4 μM or by an antisense nucleic acid compound of 9 nucleotides containing one mismatched nucleotide (i.e. with 8 complementary nucleotides) if used at a final concentration of 20 μM. For example, MA502K(5C5) (SEQ ID NO:185) corresponds to the former case and MA501I(4C4) to the latter case.

As shown above, the expression of VEGF could be inhibited even in the presence of one mismatched nucleotide every 12 nucleotides.

Test Example

The inhibitory effect of the phosphorothioate-type oligodeoxyribonucleotide expected to have the antisense nucleic acid effect on the expression of VEGF was examined by screening under the same conditions as above except that 0.8 μM or 1.875 μM nucleic acid compound was used in place of the concentration indicated in Table 6. The results are shown in Table 8.

TABLE 8

| | expression of VEGF (%) | | |
|---|---|---|---|
| sample # | 64 nM | 150 nM | SEQ ID NO: |
| A085R-S | 98 | 57 | 99 |
| A087P-S | 94 | 58 | 100 |
| A213N-S | 71 | 65 | 123 |
| A217N-S | — | 33 | 124 |
| A227-S | 45 | — | 37 |
| A237N-S | — | 8 | 125 |
| A248N-S | — | 18 | 128 |
| A261N-S | 66 | 50 | 130 |
| A287-S | 59 | — | 47 |
| A299N-S | — | 10 | 136 |
| A311-S | 56 | — | 51 |
| A313N-S | — | 41 | 138 |
| A317N-S | — | 39 | 139 |
| A321N-S | 55 | 34 | 141 |
| A407-S | 64 | — | 67 |
| A419-S | 39 | — | 69 |
| A422N-S | — | 7 | 155 |
| A461-S | 28 | — | 76 |
| RA143-S | — | 78 | 94 |
| R3126-S | 98 | 76 | 10 |

In Table 8, "64 nM" is the final concentration of the nucleic acid compound when 0.8 μM nucleic acid compound was used in the composition of Table 6 and "150 nM" means the final concentration when 1.875 μM was used. In Table 8, "S" after the hyphen "-" indicates that the sample is a phosphorothioate type. As is evident from Table 8, the inhibitory effect of the phosphorothioate-type antisense nucleic acid compound on the expression of VEGF was significantly lower than in the presence of the control nucleic acid compound (RA143-S (SEQ ID NO:94) and R3126-S (SEQ ID NO:10)). Because the expression percentages of VEGF in the presence of 150 nM RA143-S (SEQ ID NO:94) and R3126-S (SEQ ID NO:10) as the control nucleic acid compounds were 78% and 76%, respectively as shown in Table 8, the inhibitory effect of nucleic acid compounds such as A085R-S (SEQ ID NO:99) (57 % expression) and A237N-S (SEQ ID NO:125) (8% expression) is considered effective. Hence, the phosphorothioate-type oligodeoxyribonucleotide also exhibits the antisense nucleic acid effect. R3126-S (SEQ ID NO:10) in Table 8 has a phosphorothioate-type oligodeoxyribonucleotide as shown in SEQ ID NO:10, which is a random sequence towards the VEGF gene.

The phosphorothioate-type oligodeoxyribonucleotides expected to have the antisense nucleic acid effect were used as the antisense nucleic acid compound to examine their inhibitory effect on the expression of VEGF in cultured cell. This experiment was carried out in a cell culture system using human lung cancer-derived A549 cells under sterized conditions, on the basis of the method described in the literature (M. -Y. Chiang et al., The Journal of Biological Chemistry, Vol. 266, No. 27, pp. 18162 to 18172 (1991)), as follows:

A549 cells were placed in a 48- or 96-well plate and incubated at 37° C. under a 5% $CO_2$ atmosphere in Dulbecco's modified Eagle medium (DMEM) containing 10% fetal bovine serum until it became confluent. After removal of the medium, the plate was washed with Opti-MEM medium, and Opti-MEM containing 20 $\mu$g/ml lipofectin reagent (available from GIBCO BRL) was put in an amount of 380 $\mu$l (when a 48-well plate was used) to each well. 20 $\mu$M phosphorothioate-type oligodeoxyribonucleotide in physiological saline was put in an amount of 20 $\mu$l (when a 48-well plate was used) to each well, and the plate was incubated at 37° C. for 4 hours under a 5% $CO_2$ atmosphere. The solution was removed, and the plate was washed with DMEM medium containing 10% fetal bovine serum. Then, DMEM medium containing 10% fetal bovine serum was put in an amount of 380 $\mu$l (when a 48-well plate was used) to each well, and then 20 $\mu$M phosphorothioate-type oligodeoxyribonucleotide in physiological saline was put in an amount of 20 $\mu$l (when a 48-wells plate was used) to each well. The plate was incubated at 37° C. for 20 hours under a 5% $CO_2$ atmosphere. Thereafter, the VEGF in the medium was determined as described above in (4) Confirmation of expression of VEGF, (i) Enzyme immunoassays. The expression of VEGF in the presence of the phosphorothioate-type oligodeoxyribonucleotide was determined by making a comparison with the expression (assumed to be 100%) of VEGF in the absence of said compound. The results are shown in Table 9.

TABLE 9

| sample # | expression of VEGF (%) |
| --- | --- |
| A085R-S (SEQ ID NO:99) | 63 ± 5 |
| A087P-S (SEQ ID NO:100) | 65 ± 1 |
| A227-S (SEQ ID NO:37) | 70 ± 4 |
| A287-S (SEQ ID NO:47) | 60 ± 0 |
| A311-S (SEQ ID NO:51) | 66 ± 6 |
| A419-S (SEQ ID NO:69) | 54 ± 9 |
| S085R-S | 92 ± 1 |
| RA143-S (SEQ ID NO:94) | 85 ± 1 |

As shown in Table 9, the amount of VEGF expressed in the presence of the phosphorothioate-type oligodeoxyribonucleotide as the antisense nucleic acid is lower than in the presence of the phosphorothioate-type oligodeoxyribonucleotide of the random sequence (RA143-S) (SEQ ID NO:94) or the sense sequence (s085R-S). That is, because as shown in Table 2, the expression percentages of VEGF in the presence of S085R-S and RA143-S (SEQ ID NO:94) as the control nucleic acids were 92% and 85%, respectively, the inhibitory effect of samples such as A085R-S (SEQ ID NO:99) (63% expression) and A419-S (SEQ ID NO:(54% expression) etc. is considered to be effective.

From the foregoing, it was found that the phosphorothioate-type oligodeoxyribonucleotides having the nucleotide sequences selected in the screening in the cell-free system can be used to inhibit the expression of VEGF in the cultured cells, as well.

The phosphorothioate-type oligodeoxyribonucleotides expected to have the antisense nucleic acid effect were used as the antisense nucleic acid to examine their inhibitory effect on the expression of VEGF in animals. As the indicator of the inhibitory effect, the growth of human fibroblast-derived HT1080 cells transplanted intracutaneously in nude mice was used as described below. $1 \times 10^6$ HT1080 cells derived from human fibroblast, obtained by tissue culture in Dulbecco's modified Eagle medium (DMEM), were transplanted intracutaneously in each 4-week-old male nude mouse (BALB/C nu/nu) (Day 0). 100 $\mu$l each of 100 $\mu$M phosphorothioate-type nucleic acid compound A419-S (SEQ ID NO:69) in physiological saline, 100 $\mu$M phosphorothioate-type nucleic acid compound RA419-S in physiological saline, and physiological saline only were given respectively to mice once per day. A419-S (SEQ ID NO:69) is the same compound designated A419-S (SEQ ID NO:69) in Table 8, and its nucleotide sequence is shown in A419 (SEQ ID NO:69) in Table 1. RA419-S (SEQ ID NO:11) is identical in nucleotide composition with A419-S (SEQ ID NO:69) in Table 1, but not complementary to the nucleotide sequence of the VEGF gene, and its nucleotide sequence is shown in SEQ ID NO:11.

After intracutaneous transplantation of HT1080 cells, each nude mouse was examined every about 3 days for body weight and tumor size and simultaneously a picture was taken. The group given the antisense nucleic acid compound (A419-S) indicated a smaller tumor size than the group given RA419-S (SEQ ID NO:11) or physiological saline. As an example, the results on Day 19 are shown in Table 10.

TABLE 10

| | tumor size (19 days after transplantation) |
| --- | --- |
| A419-S (SEQ ID NO:69) | 740 ± 150 mm³ (n = 3) |
| RA419-S (SEQ ID NO:11) | 1470 ± 870 mm³ (n = 3) |
| control (physiological saline) | 1260 ± 320 mm³ (n = 2) |

From the foregoing, it was found that the phosphorothioate-type oligodeoxyribonucleotide selected by screening in the cell-free and cultured-cell systems can be used to inhibit tumor growth in experimental animals. This inhibition of tumor growth can be considered to result from the inhibitory effect of the antisense nucleic acid on the expression of VEGF.

From a large number of these examples, it could be estimated that the antisense nucleic compound having a nucleotide sequence complementary to 8 or more nucleotides within the core region exerts a strong inhibitory effect on the expression of VEGF. In view of the role of VEGF as a tumor angiogenic factor in vivo (K. J. Kim et al., Nature, Vol. 362, April 29 issue, pp. 841–844 (1993); and S. Kondo et al., Biochemical and Biophysical Research Communications, Vol. 194, No. 3, pp. 1234–1241 (1993)), the antisense nucleic acid compound having a nucleotide sequence complementary to 8 or more nucleotides in the core region is useful as a therapeutic agent such as anticancer drug to inhibit the growth of solid tumor cells or as a diagnostic agent for cancers.

Industrial Applicability

According to the present invention, there is provided an antisense nucleic acid compound inhibiting the expression of the gene coding for VEGF.

The antisense nucleic acid compound of the present invention can inhibit the growth of solid tumors by inhibiting the expression of VEGF i.e. a factor facilitating the arrival of blood vessels at the solid tumors. Therefore, it can be used as an anticancer drug to inhibit the growth of solid tumor cells. Because VEGF is involved in rheumatoid arthritis and diabetes as well, the antisense nucleic acid compound of the present invention can also be used as an therapeutic agent for such diseases.

Further, the antisense nucleic acid compound of the present invention can be used as a diagnostic agent for detection of solid tumor cells as well as for diagnosis of rheumatoid arthritis and diabetes.

What is claimed is:

1. An antisense nucleic acid compound consisting of a nucleotide sequence complementary to at least 8 contiguous nucleotides in the nucleic acid sequence defined by any of SEQ ID NOS: 4, 6, 7, or 8; wherein said antisense nucleic acid compound inhibits the expression of vascular endothelial growth factor.

2. An antisense nucleic acid compound consisting of a nucleotide sequence complementary to at least 10 contiguous nucleotides in the nucleic acid sequence defined by any of SEQ ID NOS: 4, 6, 7, or 8; wherein said antisense nucleic acid compound inhibits the expression of vascular endothelial growth factor.

3. An antisense nucleic acid compound consisting of at least 10 contiguous nucleotides having nine or more nucleotides complementary to, and one nucleotide mismatched to, the nucleic acid sequence defined by any of SEQ ID NOS: 2, 3, 4, 5, 6, 7, 8, or 9, and which inhibits the expression of vascular endothelial growth factor.

4. An antisense nucleic acid compound consisting of 12 or more contiguous nucleotides having 11 or more nucleotides complementary to, and 1 nucleotide mismatched to, the nucleic acid sequence defined by any of SEQ ID NOS: 2, 3, 4, 5, 6, 7, 8, or 9, and which inhibits the expression of vascular endothelial growth factor.

5. A pharmaceutical composition comprising as an active ingredient an antisense nucleic acid compound according to any of claims 1, 2, 3, or 4 and a pharmaceutically acceptable carrier.

6. A diagnostic agent comprising as an active ingredient an antisense nucleic acid compound according to any of claims 1, 2, 3 or 4 and a pharmaceutically acceptable carrier.

7. An antisense nucleic acid compound which inhibits the expression of vascular endothelial growth factor and which consists of a nucleic acid sequence selected from the group consisting of SEQ ID NOS: 15, 23, 24, 25, 26, 29, 30, 31, 32, 37, 41, 42, 43, 46, 47, 49, 50, 51, 57, 58, 59, 63, 64, 65, 66, 67, 68, 69, 70, 71, 72, 73, 74, 75, 76, 77, 78, 79, 80, 81, 82, 83, 84, 85, 86, 90, 99, 100, 101, 102, 103, 110, 111, 112, 114, 117, 118, 119, 120, 121, 123, 124, 125, 128, 129, 130, 131, 132, 134, 135, 136, 137, 138, 139, 141, 146, 147, 148, 153, 154, 155, 156, 157, 158, 159, 160, 161, 162, 163, 164, 165, 167, 169, 170, 171, 172, 173, 175, 176, 177, 178, 179, 180, 181, 182, 183, 184 185, and combinations thereof.

8. An antisense nucleic acid compound which includes the expression of vascular endothelial growth factor to a level of about 10% or less and which consists of a nucleic acid sequence selected from the group consisting of GCTCTATC and CTCTCTCTT.

9. An antisense nucleic acid compound consisting of a nucleotide sequence complementary to a nucleic acid sequence defined by any of SEQ ID NOS: 2, 3, 4, 5, 6, 7, 8 or 9 wherein said antisense nucleic acid compound inhibits the expression of vascular endothelial growth factor.

10. An antisense nucleic acid compound which inhibits the expression of vascular endothelial growth factor and which consists of a nucleic acid sequence selected from the group consisting of SEQ ID NOS: 13, 17, 18, 19, 20, 21, 22, 27, 33, 34, 35, 36, 38, 39, 40, 44, 45, 48, 49, 52, 53, 56, 60, 61, 62, 87, 89, 92, 95, 97, 98, 104, 105, 106, 107, 108, 115, 116, 122, 126, 127, 140, 142, 144, 145, 149, 150, 151, 152, 174, and combinations thereof.

11. An antisense nucleic acid compound consisting of a nucleotide sequence complementary to 8 to 10 contiguous nucleotides in the nucleic acid sequence defined by any of SEQ ID NOS: 2, 3, 5, or 9; wherein said antisense nucleic acid compound inhibits the expression of vascular endothelial growth factor.

12. An antisense nucleic acid compound consisting of a nucleotide sequence complementary to 10 to 12 contiguous nucleotides in the nucleic acid sequence defined by any of SEQ ID NOS: 2, 3, 5, or 9; wherein said antisense nucleic acid compound inhibits the expression of vascular endothelial growth factor.

13. An antisense nucleic acid compound consisting of a nucleotide sequence complementary to at least 8 contiguous nucleotides in the nucleic acid sequence defined by any of SEQ ID NOS: 2, 3, 5, or 9; wherein said antisense nucleic acid compound inhibits the expression of vascular endothelial growth factor.

14. An antisense nucleic acid compound consisting of a nucleotide sequence complementary to at least 10 contiguous nucleotides in the nucleic acid sequence defined by any of SEQ ID NOS: 2, 3, 5, or 9; wherein said antisense nucleic acid compound inhibits the expression of vascular endothelial growth factor.

15. An antisense nucleic acid compound according to any of claims 1, 2, 3, 4, 13, or 14; said antisense nucleic acid compound having from 14 to 30 nucleotides.

16. A pharmaceutical composition comprising the antisense nucleic acid compound according to any of claims 7, 8, 9, 10, 11, 12, 13, or 14 and a pharmaceutically acceptable carrier.

17. A diagnostic agent comprising as active ingredient the antisense nucleic acid compound according to any of claims 7, 8, 9, 10, 11, 12, 13, or 14 and a pharmaceutically acceptable carrier.

18. A method of inhibiting the expression of a vascular endothelial growth factor, comprising administering to a subject an antisense nucleic acid compound consisting of a nucleotide sequence complementary to at least 8 contiguous nucleotides in the nucleic acid sequence defined by any of SEQ ID NOS: 4, 6, 7, or 8; in a physiologically acceptable carrier, diluent, or excipient thereby inhibiting the expression of the vascular endothelial growth factor.

19. A method of inhibiting the expression of a vascular endothelial growth factor, comprising administering to a subject an antisense nucleic acid compound consisting of a nucleotide sequence complementary to at least 10 contiguous nucleotides in the nucleic acid sequence defined by any of SEQ ID NOS: 4, 6, 7, or 8; in a physiologically acceptable carrier, diluent, or excipient thereby inhibiting the expression of the vascular endothelial growth factor.

20. A method of inhibiting the expression of a vascular endothelial growth factor, comprising administering to a subject the antisense nucleic acid compound according to any one of claims 1, 2, 3, 4, 7, 8, 9, 10, 11, 12, 13 or 14 in a physiologically acceptable carrier, diluent, or excipient thereby inhibiting the expression of the vascular endothelial growth factor.

21. A method of inhibiting the expression of a vascular endothelial growth factor, comprising administering to a subject an antisense nucleic acid compound consisting of a nucleotide sequence complementary to 8 to 10 contiguous nucleotides in the nucleic acid sequence defined by any of SEQ ID NOS: 2, 3, 5, or 9, in a physiologically acceptable carrier, diluent, or excipient thereby inhibiting the expression of the vascular endothelial growth factor.

22. A method of inhibiting the expression of a vascular endothelial growth factor, comprising administering to a subject an antisense nucleic acid compound consisting of a nucleotide sequence complementary to 10 to 12 contiguous nucleotides in the nucleic acid sequence defined by any of SEQ ID NOS: 2, 3, 5, or 9, in a physiologically acceptable carrier, diluent or excipient thereby inhibiting the expression of the vascular endothelial growth factor.

23. A method of inhibiting the expression of a vascular endothelial growth factor, comprising administering to a subject an antisense nucleic acid compound consisting of a nucleotide sequence complementary to at least 8 contiguous nucleotides in the nucleic acid sequence defined by any of SEQ ID NOS: 2, 3, 5, or 9, in a physiologically acceptable carrier, diluent, or excipient thereby inhibiting the expression of the vascular endothelial growth factor.

24. A method of inhibiting the expression of a vascular endothelial growth factor, comprising administering to a subject an antisense nucleic acid compound consisting of a nucleotide sequence complementary to at least 10 contiguous nucleotides in the nucleic acid sequence defined by any of SEQ ID NOS: 2, 3, 5, or 9, in a physiologically acceptable carrier, diluent, or excipient thereby inhibiting the expression of the vascular endothelial growth factor.

25. The method according to any of claims 18, 19, 23, or 24; wherein said antisense nucleic acid compound has 14 to 30 nucleotides.

* * * * *

SEQUENCE LISTING (1) GENERAL INFORMATION:

(iii) NUMBER OF SEQUENCES: 185

(2) INFORMATION FOR SEQ ID NO: 1:

(i) SEQUENCE CHARACTERISTICS:
      (A) LENGTH: 774 base pairs
      (B) TYPE: nucleic acid
      (C) STRANDEDNESS: single
      (D) TOPOLOGY: linear (ii) MOLECULE TYPE: cDNA to mRNA (xi) SEQUENCE DESCRIPTION: SEQ ID NO: 1:

```
TTATGTATCA TACACATACG ATTTAGGTGA CACTATAGAA                    40
TACAAGCTTA TGCATGCGGC CGCATCTAGA GGGCCCGGCC                    80
CCGGTCGGGC CTCCGAAACC ATGAACTTTC TGCTGTCTTG                   120
GGTGCATTGG AGCCTTGCCT TGCTGCTCTA CCTCCACCAT                   160
GCCAAGTGGT CCCAGGCTGC ACCCATGGCA GAAGGAGGAG                   200
GGCAGAATCA TCACGAAGTG GTGAAGTTCA TGGATGTCTA                   240
TCAGCGCAGC TACTGCCATC CAATCGAGAC CCTGGTGGAC                   280
ATCTTCCAGG AGTACCCTGA TGAGATCGAG TACATCTTCA                   320
AGCCATCCTG TGTGCCCCTG ATGCGATGCG GGGGCTGCTG                   360
CAATGACGAG GGCCTGGAGT GTGTGCCCAC TGAGGAGTCC                   400
AACATCACCA TGCAGATTAT GCGGATCAAA CCTCACCAAG                   440
GCCAGCACAT AGGAGAGATG AGCTTCCTAC AGCACAACAA                   480
ATGTGAATGC AGACCAAAGA AAGATAGAGC AAGACAAGAA                   520
AAATGTGACA AGCCGAGGCG GTGAGCCGGG CAGGAGGAAG                   560
GAGCCTCCCT CAGGGTTTCG GGAACCAGAT CCACTAGTTC                   600
TAGATGCATG CTCGAGCGGC CGCCAGTGTG ATGGATATCT                   640
GCAGAATTCC AGCACACTGG CCGTTACTAG TGGATCCGAG                   680
CTCCCAAAAA AAAAAAAAA AAAAAAAAAA AAAAACCGAA                    720
TTAATTCGTA ATCATGGTCA TAGCTGTTTC CTGTGTGAAA                   760
TTGTTATCCG CTCA                                               774
```

(2) INFORMATION FOR SEQ ID NO: 2:

(i) SEQUENCE CHARACTERISTICS:
      (A) LENGTH: 14 base pairs
      (B) TYPE: nucleic acid
      (C) STRANDEDNESS: single
      (D) TOPOLOGY: linear

```
        (ii) MOLECULE TYPE: cDNA to mRNA (xi) SEQUENCE DESCRIPTION: SEQ ID NO: 2:

GAAACCATGA ACTT                                                          14

(2) INFORMATION FOR SEQ ID NO: 3:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: cDNA to mRNA (xi) SEQUENCE DESCRIPTION: SEQ ID NO: 3:

TACCTCCACC ATGCCAAGTG GTCCCA                                             26

(2) INFORMATION FOR SEQ ID NO: 4:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: cDNA to mRNA (xi) SEQUENCE DESCRIPTION: SEQ ID NO: 4:

ATGGCAGAAG GAGGAGGGCA GAATCA                                             26

(2) INFORMATION FOR SEQ ID NO: 5:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: cDNA to mRNA (xi) SEQUENCE DESCRIPTION: SEQ ID NO: 5:

TGGTGAAGTT CATGGATGTC TATCAG                                             26

(2) INFORMATION FOR SEQ ID NO: 6:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA to mRNA (xi) SEQUENCE DESCRIPTION: SEQ ID NO: 6:

TGCCATCCAA TCGAGACCCT GGT                                                23

(2) INFORMATION FOR SEQ ID NO: 7:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: cDNA to mRNA (xi) SEQUENCE DESCRIPTION: SEQ ID NO: 7:
```

```
CAGGAGTACC CTGATGAGAT CGAGTACATC TTCAAGCCAT CC                           42
```

(2) INFORMATION FOR SEQ ID NO: 8:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA to mRNA (xi) SEQUENCE DESCRIPTION: SEQ ID NO: 8:

```
GCTGCAATGA CGAGGG                                                       16
```

(2) INFORMATION FOR SEQ ID NO: 9:

(i) SEQUENCE CHARACTERISTICS:
        (A) LENGTH: 146 base pairs
        (B) TYPE: nucleic acid
        (C) STRANDEDNESS: single
        (D) TOPOLOGY: linear (ii) MOLECULE TYPE: cDNA to mRNA (xi) SEQUENCE DESCRIPTION: SEQ ID NO: 9:

```
ACTGAGGAGT CCAACATCAC CATGCAGATT ATGCGGATCA                              40

AACCTCACCA AGGCCAGCAC ATAGGAGAGA TGAGCTTCCT                              80

ACAGCACAAC AAATGTGAAT GCAGACCAAA GAAAGATAGA                             120

GCAAGACAAG AAAAATGTGA CAAGCC                                            146
```

(2) INFORMATION FOR SEQ ID NO: 10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 10:

```
AAAAAAACAA AAACAACAAA                                                   20
```

(2) INFORMATION FOR SEQ ID NO: 11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 11:

```
CTAGACTGTG TGTTCTGGAG                                                   20
```

(2) INFORMATION FOR SEQ ID NO: 12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
            (A) DESCRIPTION:   /desc = "synthetic DNA"

(xi) SEQUENCE DESCRIPTION: SEQ ID NO: 12:

TCGGAGGCCC GACCGGGGCC                                                        20

(2) INFORMATION FOR SEQ ID NO: 13:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "synthetic DNA"

(xi) SEQUENCE DESCRIPTION: SEQ ID NO: 13:

ATGGTTTCGG AGGCCCGACC                                                        20

(2) INFORMATION FOR SEQ ID NO: 14:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "synthetic DNA"

(xi) SEQUENCE DESCRIPTION: SEQ ID NO: 14:

AAGTTCATGG TTTCGGAGGC                                                        20

(2) INFORMATION FOR SEQ ID NO: 15:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "synthetic DNA"

(xi) SEQUENCE DESCRIPTION: SEQ ID NO: 15:

AGCAGAAAGT TCATGGTTTC                                                        20

(2) INFORMATION FOR SEQ ID NO: 16:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "synthetic DNA"

(xi) SEQUENCE DESCRIPTION: SEQ ID NO: 16:

CAAGACAGCA GAAAGTTCAT                                                        20

(2) INFORMATION FOR SEQ ID NO: 17:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
             (A) DESCRIPTION:    /desc = "synthetic DNA"

(xi) SEQUENCE DESCRIPTION: SEQ ID NO: 17:

TGCACCCAAG ACAGCAGAAA                                                          20

(2) INFORMATION FOR SEQ ID NO: 18:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid
             (A) DESCRIPTION:    /desc = "synthetic DNA"

(xi) SEQUENCE DESCRIPTION: SEQ ID NO: 18:

CTCCAATGCA CCCAAGACAG                                                          20

(2) INFORMATION FOR SEQ ID NO: 19:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid
             (A) DESCRIPTION:    /desc = "synthetic DNA"

(xi) SEQUENCE DESCRIPTION: SEQ ID NO: 19:

GCAAGGCTCC AATGCACCCA                                                          20

(2) INFORMATION FOR SEQ ID NO: 20:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid
             (A) DESCRIPTION:    /desc = "synthetic DNA"

(xi) SEQUENCE DESCRIPTION: SEQ ID NO: 20:

AGCAAGGCAA GGCTCCAATG                                                          20

(2) INFORMATION FOR SEQ ID NO: 21:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid
             (A) DESCRIPTION:    /desc = "synthetic DNA"

(xi) SEQUENCE DESCRIPTION: SEQ ID NO: 21:

TAGAGCAGCA AGGCAAGGCT                                                          20

(2) INFORMATION FOR SEQ ID NO: 22:

(i) SEQUENCE CHARACTERISTICS:
             (A) LENGTH: 20 base pairs
             (B) TYPE: nucleic acid
             (C) STRANDEDNESS: single

```
        (D) TOPOLOGY: linear (ii) MOLECULE TYPE: other nucleic acid
        (A) DESCRIPTION:    /desc = "synthetic DNA"

(xi) SEQUENCE DESCRIPTION: SEQ ID NO: 22:

TGGAGGTAGA GCAGCAAGGC                                              20

(2) INFORMATION FOR SEQ ID NO: 23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:    /desc = "synthetic DNA"

(xi) SEQUENCE DESCRIPTION: SEQ ID NO: 23:

GCATGGTGGA GGTAGAGCAG                                              20

(2) INFORMATION FOR SEQ ID NO: 24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:    /desc = "synthetic DNA"

(xi) SEQUENCE DESCRIPTION: SEQ ID NO: 24:

CACTTGGCAT GGTGGAGGTA                                              20

(2) INFORMATION FOR SEQ ID NO: 25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:    /desc = "synthetic DNA"

(xi) SEQUENCE DESCRIPTION: SEQ ID NO: 25:

TGGGACCACT TGGCATGGTG                                              20

(2) INFORMATION FOR SEQ ID NO: 26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:    /desc = "synthetic DNA"

(xi) SEQUENCE DESCRIPTION: SEQ ID NO: 26:

GCAGCCTGGG ACCACTTGGC                                              20

(2) INFORMATION FOR SEQ ID NO: 27:

(i) SEQUENCE CHARACTERISTICS:
        (A) LENGTH: 20 base pairs
        (B) TYPE: nucleic acid
```

(C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 27:

ATGGGTGCAG CCTGGGACCA                                              20

(2) INFORMATION FOR SEQ ID NO: 28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 28:

TCTGCCATGG GTGCAGCCTG                                              20

(2) INFORMATION FOR SEQ ID NO: 29:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 29:

CCTCCTTCTG CCATGGGTGC                                              20

(2) INFORMATION FOR SEQ ID NO: 30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 30:

TGCCCTCCTC CTTCTGCCAT                                              20

(2) INFORMATION FOR SEQ ID NO: 31:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 31:

TGATTCTGCC CTCCTCCTTC                                              20

(2) INFORMATION FOR SEQ ID NO: 32:

(i) SEQUENCE CHARACTERISTICS:
        (A) LENGTH: 20 base pairs (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 32:

TCGTGATGAT TCTGCCCTCC                                           20

(2) INFORMATION FOR SEQ ID NO: 33:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 33:

ACCACTTCGT GATGATTCTG                                           20

(2) INFORMATION FOR SEQ ID NO: 34:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 34:

AACTTCACCA CTTCGTGATG                                           20

(2) INFORMATION FOR SEQ ID NO: 35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 35:

TCCATGAACT TCACCACTTC                                           20

(2) INFORMATION FOR SEQ ID NO: 36:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 36:

TAGACATCCA TGAACTTCAC                                           20

(2) INFORMATION FOR SEQ ID NO: 37:

(i) SEQUENCE CHARACTERISTICS:

(A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 37:

CGCTGATAGA CATCCATGAA                                                   20

(2) INFORMATION FOR SEQ ID NO: 38:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 38:

TAGCTGCGCT GATAGACATC                                                   20

(2) INFORMATION FOR SEQ ID NO: 39:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 39:

TGGCAGTAGC TGCGCTGATA                                                   20

(2) INFORMATION FOR SEQ ID NO: 40:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 40:

ATTGGATGGC AGTAGCTGCG                                                   20

(2) INFORMATION FOR SEQ ID NO: 41:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 41:

GTCTCGATTG GATGGCAGTA                                                   20

(2) INFORMATION FOR SEQ ID NO: 42:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "synthetic DNA"

(xi) SEQUENCE DESCRIPTION: SEQ ID NO: 42:

ACCAGGGTCT CGATTGGATG                                                     20

(2) INFORMATION FOR SEQ ID NO: 43:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "synthetic DNA"

(xi) SEQUENCE DESCRIPTION: SEQ ID NO: 43:

ATGTCCACCA GGGTCTCGAT                                                     20

(2) INFORMATION FOR SEQ ID NO: 44:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "synthetic DNA"

(xi) SEQUENCE DESCRIPTION: SEQ ID NO: 44:

TGGAAGATGT CCACCAGGGT                                                     20

(2) INFORMATION FOR SEQ ID NO: 45:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "synthetic DNA"

(xi) SEQUENCE DESCRIPTION: SEQ ID NO: 45:

TACTCCTGGA AGATGTCCAC                                                     20

(2) INFORMATION FOR SEQ ID NO: 46:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "synthetic DNA"

(xi) SEQUENCE DESCRIPTION: SEQ ID NO: 46:

TCAGGGTACT CCTGGAAGAT                                                     20

(2) INFORMATION FOR SEQ ID NO: 47:

```
    (i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 47:

ATCTCATCAG GGTACTCCTG                                                   20

(2) INFORMATION FOR SEQ ID NO: 48:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 48:

TACTCGATCT CATCAGGGTA                                                   20

(2) INFORMATION FOR SEQ ID NO: 49:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 49:

AAGATGTACT CGATCTCATC                                                   20

(2) INFORMATION FOR SEQ ID NO: 50:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 50:

GGCTTGAAGA TGTACTCGAT                                                   20

(2) INFORMATION FOR SEQ ID NO: 51:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 51:

CAGGATGGCT TGAAGATGTA                                                   20
```

(2) INFORMATION FOR SEQ ID NO: 52:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  /desc = "synthetic DNA"

(xi) SEQUENCE DESCRIPTION: SEQ ID NO: 52:

GGCACACAGG ATGGCTTGAA                                          20

(2) INFORMATION FOR SEQ ID NO: 53:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  /desc = "synthetic DNA"

(xi) SEQUENCE DESCRIPTION: SEQ ID NO: 53:

ATCAGGGGCA CACAGGATGG                                          20

(2) INFORMATION FOR SEQ ID NO: 54:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  /desc = "synthetic DNA"

(xi) SEQUENCE DESCRIPTION: SEQ ID NO: 54:

CATCGCATCA GGGGCACACA                                          20

(2) INFORMATION FOR SEQ ID NO: 55:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  /desc = "synthetic DNA"

(xi) SEQUENCE DESCRIPTION: SEQ ID NO: 55:

CCCCCGCATC GCATCAGGGG                                          20

(2) INFORMATION FOR SEQ ID NO: 56:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  /desc = "synthetic DNA"

(xi) SEQUENCE DESCRIPTION: SEQ ID NO: 56:

CAGCAGCCCC CGCATCGCAT                                          20

(2) INFORMATION FOR SEQ ID NO: 57:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 57:

TCATTGCAGC AGCCCCCGCA                                                    20

(2) INFORMATION FOR SEQ ID NO: 58:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 58:

CCCTCGTCAT TGCAGCAGCC                                                    20

(2) INFORMATION FOR SEQ ID NO: 59:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 59:

TCCAGGCCCT CGTCATTGCA                                                    20

(2) INFORMATION FOR SEQ ID NO: 60:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 60:

ACACACTCCA GGCCCTCGTC                                                    20

(2) INFORMATION FOR SEQ ID NO: 61:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 61:

GTGGGCACAC ACTCCAGGCC                                                    20

(2) INFORMATION FOR SEQ ID NO: 62:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 62:

TCCTCAGTGG GCACACACTC                                                    20

(2) INFORMATION FOR SEQ ID NO: 63:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 63:

TTGGACTCCT CAGTGGGCAC                                                    20

(2) INFORMATION FOR SEQ ID NO: 64:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 64:

GTGATGTTGG ACTCCTCAGT                                                    20

(2) INFORMATION FOR SEQ ID NO: 65:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 65:

TGCATGGTGA TGTTGGACTC                                                    20

(2) INFORMATION FOR SEQ ID NO: 66:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 66:

```
ATAATCTGCA TGGTGATGTT                                                    20

(2) INFORMATION FOR SEQ ID NO: 67:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 67:

ATCCGCATAA TCTGCATGGT                                                    20

(2) INFORMATION FOR SEQ ID NO: 68:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 68:

GGTTTGATCC GCATAATCTG                                                    20

(2) INFORMATION FOR SEQ ID NO: 69:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 69:

TGGTGAGGTT TGATCCGCAT                                                    20

(2) INFORMATION FOR SEQ ID NO: 70:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 70:

TGGCCTTGGT GAGGTTTGAT                                                    20

(2) INFORMATION FOR SEQ ID NO: 71:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 71:
```

ATGTGCTGGC CTTGGTGAGG                                          20

(2) INFORMATION FOR SEQ ID NO: 72:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 72:

TCTCCTATGT GCTGGCCTTG                                          20

(2) INFORMATION FOR SEQ ID NO: 73:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 73:

CTCATCTCTC CTATGTGCTG                                          20

(2) INFORMATION FOR SEQ ID NO: 74:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 74:

AGGAAGCTCA TCTCTCCTAT                                          20

(2) INFORMATION FOR SEQ ID NO: 75:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 75:

TGCTGTAGGA AGCTCATCTC                                          20

(2) INFORMATION FOR SEQ ID NO: 76:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 76:

TTGTTGTGCT GTAGGAAGCT                                               20

(2) INFORMATION FOR SEQ ID NO: 77:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 77:

TCACATTTGT TGTGCTGTAG                                               20

(2) INFORMATION FOR SEQ ID NO: 78:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 78:

CTGCATTCAC ATTTGTTGTG                                               20

(2) INFORMATION FOR SEQ ID NO: 79:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 79:

TTTGGTCTGC ATTCACATTT                                               20

(2) INFORMATION FOR SEQ ID NO: 80:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 80:

TCTTTCTTTG GTCTGCATTC                                               20

(2) INFORMATION FOR SEQ ID NO: 81:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 81:

GCTCTATCTT TCTTTGGTCT                                         20

(2) INFORMATION FOR SEQ ID NO: 82:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 82:

TGTCTTGCTC TATCTTTCTT                                         20

(2) INFORMATION FOR SEQ ID NO: 83:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 83:

TTTTCTTGTC TTGCTCTATC                                         20

(2) INFORMATION FOR SEQ ID NO: 84:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 84:

TCACATTTTT CTTGTCTTGC                                         20

(2) INFORMATION FOR SEQ ID NO: 85:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 85:

GGCTTGTCAC ATTTTTCTTG                                         20

(2) INFORMATION FOR SEQ ID NO: 86:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (A) DESCRIPTION:   /desc = "synthetic DNA"

(xi) SEQUENCE DESCRIPTION: SEQ ID NO: 86:

CGCCTCGGCT TGTCACATTT                                               20

(2) INFORMATION FOR SEQ ID NO: 87:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 87:

GCTCACCGCC TCGGCTTGTC                                               20

(2) INFORMATION FOR SEQ ID NO: 88:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 88:

TGCCCGGCTC ACCGCCTCGG                                               20

(2) INFORMATION FOR SEQ ID NO: 89:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 89:

TCCTCCTGCC CGGCTCACCG                                               20

(2) INFORMATION FOR SEQ ID NO: 90:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 90:

GCTCCTTCCT CCTGCCCGGC                                               20

(2) INFORMATION FOR SEQ ID NO: 91:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
                 (A) DESCRIPTION:   /desc = "synthetic DNA"

(xi) SEQUENCE DESCRIPTION: SEQ ID NO: 91:

AGGGAGGCTC CTTCCTCCTG                                                      20

(2) INFORMATION FOR SEQ ID NO: 92:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "synthetic DNA"

(xi) SEQUENCE DESCRIPTION: SEQ ID NO: 92:

ATGAACTTTC TGCTGTCTTG                                                      20

(2) INFORMATION FOR SEQ ID NO: 93:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "synthetic DNA"

(xi) SEQUENCE DESCRIPTION: SEQ ID NO: 93:

AACTATAAGC ACGGTAACGA                                                      20

(2) INFORMATION FOR SEQ ID NO: 94:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "synthetic DNA"

(xi) SEQUENCE DESCRIPTION: SEQ ID NO: 94:

GAAGTGAGCG TGAGCGTGAG                                                      20

(2) INFORMATION FOR SEQ ID NO: 95:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "synthetic DNA"

(xi) SEQUENCE DESCRIPTION: SEQ ID NO: 95:

CTCACGCTCA CGCTCACTTC                                                      20

(2) INFORMATION FOR SEQ ID NO: 96:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION:    /desc = "synthetic DNA"

(xi) SEQUENCE DESCRIPTION: SEQ ID NO: 96:

TTTTTTTTTT TTTTTTTTTT                                                    20

(2) INFORMATION FOR SEQ ID NO: 97:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: other nucleic acid
            (A) DESCRIPTION:    /desc = "synthetic DNA"

(xi) SEQUENCE DESCRIPTION: SEQ ID NO: 97:

TCGGAGGCCC GACC                                                          14

(2) INFORMATION FOR SEQ ID NO: 98:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: other nucleic acid
            (A) DESCRIPTION:    /desc = "synthetic DNA"

(xi) SEQUENCE DESCRIPTION: SEQ ID NO: 98:

TTTCGGAGGC CCGA                                                          14

(2) INFORMATION FOR SEQ ID NO: 99:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION:    /desc = "synthetic DNA"

(xi) SEQUENCE DESCRIPTION: SEQ ID NO: 99:

ATGGTTTCGG AGGCCCGA                                                      18

(2) INFORMATION FOR SEQ ID NO: 100:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: other nucleic acid
            (A) DESCRIPTION:    /desc = "synthetic DNA"

(xi) SEQUENCE DESCRIPTION: SEQ ID NO: 100:

ATGGTTTCGG AGGCCC                                                        16

(2) INFORMATION FOR SEQ ID NO: 101:

(i) SEQUENCE CHARACTERISTICS:
            (A) LENGTH: 14 base pairs
            (B) TYPE: nucleic acid
            (C) STRANDEDNESS: single (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 101:

ATGGTTTCGG AGGC                                                              14

(2) INFORMATION FOR SEQ ID NO: 102:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 102:

AAGTTCATGG TTTC                                                              14

(2) INFORMATION FOR SEQ ID NO: 103:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 103:

AGCAGAAAGT TCAT                                                              14

(2) INFORMATION FOR SEQ ID NO: 104:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 104:

AGACAGCAGA AAGT                                                              14

(2) INFORMATION FOR SEQ ID NO: 105:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 105:

CCAAGACAGC AGAA                                                              14

(2) INFORMATION FOR SEQ ID NO: 106:

(i) SEQUENCE CHARACTERISTICS:
        (A) LENGTH: 14 base pairs
        (B) TYPE: nucleic acid

```
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 106:

CCCAAGACAG CAGA                                                             14

(2) INFORMATION FOR SEQ ID NO: 107:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 107:

ACCCAAGACA GCAG                                                             14

(2) INFORMATION FOR SEQ ID NO: 108:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 108:

TGGAGGTAGA GCAG                                                             14

(2) INFORMATION FOR SEQ ID NO: 109:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 109:

TGGTGGAGGT AGAG                                                             14

(2) INFORMATION FOR SEQ ID NO: 110:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 110:

CTTGGCATGG TGGA                                                             14

(2) INFORMATION FOR SEQ ID NO: 111:

(i) SEQUENCE CHARACTERISTICS:
        (A) LENGTH: 14 base pairs
```

(B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 111:

CACTTGGCAT GGTG                                                         14

(2) INFORMATION FOR SEQ ID NO: 112:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 112:

CCACTTGGCA TGGT                                                         14

(2) INFORMATION FOR SEQ ID NO: 113:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 113:

ACCACTTGGC ATGG                                                         14

(2) INFORMATION FOR SEQ ID NO: 114:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 114:

GCAGCCTGGG ACCA                                                         14

(2) INFORMATION FOR SEQ ID NO: 115:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 115:

ATGGGTGCAG CCTG                                                         14

(2) INFORMATION FOR SEQ ID NO: 116:

(i) SEQUENCE CHARACTERISTICS:

(A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 116:

GCCATGGGTG CAGC                                                             14

(2) INFORMATION FOR SEQ ID NO: 117:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 117:

TCTGCCATGG GTGC                                                             14

(2) INFORMATION FOR SEQ ID NO: 118:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 118:

CCCTCCTCCT TCTG                                                             14

(2) INFORMATION FOR SEQ ID NO: 119:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 119:

TGCCCTCCTC CTTC                                                             14

(2) INFORMATION FOR SEQ ID NO: 120:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 120:

TCTGCCCTCC TCCT                                                             14

(2) INFORMATION FOR SEQ ID NO: 121:

(i) SEQUENCE CHARACTERISTICS:
                (A) LENGTH: 14 base pairs
                (B) TYPE: nucleic acid
                (C) STRANDEDNESS: single
                (D) TOPOLOGY: linear (ii) MOLECULE TYPE: other nucleic acid
                (A) DESCRIPTION:   /desc = "synthetic DNA"

(xi) SEQUENCE DESCRIPTION: SEQ ID NO: 121:

TCGTGATGAT TCTG                                                            14

(2) INFORMATION FOR SEQ ID NO: 122:

(i) SEQUENCE CHARACTERISTICS:
                (A) LENGTH: 14 base pairs
                (B) TYPE: nucleic acid
                (C) STRANDEDNESS: single
                (D) TOPOLOGY: linear (ii) MOLECULE TYPE: other nucleic acid
                (A) DESCRIPTION:   /desc = "synthetic DNA"

(xi) SEQUENCE DESCRIPTION: SEQ ID NO: 122:

ACCACTTCGT GATG                                                            14

(2) INFORMATION FOR SEQ ID NO: 123:

(i) SEQUENCE CHARACTERISTICS:
                (A) LENGTH: 14 base pairs
                (B) TYPE: nucleic acid
                (C) STRANDEDNESS: single
                (D) TOPOLOGY: linear (ii) MOLECULE TYPE: other nucleic acid
                (A) DESCRIPTION:   /desc = "synthetic DNA"

(xi) SEQUENCE DESCRIPTION: SEQ ID NO: 123:

CTTCACCACT TCGT                                                            14

(2) INFORMATION FOR SEQ ID NO: 124:

(i) SEQUENCE CHARACTERISTICS:
                (A) LENGTH: 14 base pairs
                (B) TYPE: nucleic acid
                (C) STRANDEDNESS: single
                (D) TOPOLOGY: linear (ii) MOLECULE TYPE: other nucleic acid
                (A) DESCRIPTION:   /desc = "synthetic DNA"

(xi) SEQUENCE DESCRIPTION: SEQ ID NO: 124:

TGAACTTCAC CACT                                                            14

(2) INFORMATION FOR SEQ ID NO: 125:

(i) SEQUENCE CHARACTERISTICS:
                (A) LENGTH: 14 base pairs
                (B) TYPE: nucleic acid
                (C) STRANDEDNESS: single
                (D) TOPOLOGY: linear (ii) MOLECULE TYPE: other nucleic acid
                (A) DESCRIPTION:   /desc = "synthetic DNA"

(xi) SEQUENCE DESCRIPTION: SEQ ID NO: 125:

GCTGCGCTGA TAGA                                                            14

(2) INFORMATION FOR SEQ ID NO: 126:

```
     (i) SEQUENCE CHARACTERISTICS:
         (A) LENGTH: 14 base pairs
         (B) TYPE: nucleic acid
         (C) STRANDEDNESS: single
         (D) TOPOLOGY: linear (ii) MOLECULE TYPE: other nucleic acid
         (A) DESCRIPTION:   /desc = "synthetic DNA"

(xi) SEQUENCE DESCRIPTION: SEQ ID NO: 126:

CAGTAGCTGC GCTG                                                          14

(2) INFORMATION FOR SEQ ID NO: 127:

(i) SEQUENCE CHARACTERISTICS:
         (A) LENGTH: 14 base pairs
         (B) TYPE: nucleic acid
         (C) STRANDEDNESS: single
         (D) TOPOLOGY: linear (ii) MOLECULE TYPE: other nucleic acid
         (A) DESCRIPTION:   /desc = "synthetic DNA"

(xi) SEQUENCE DESCRIPTION: SEQ ID NO: 127:

TGGCAGTAGC TGCG                                                          14

(2) INFORMATION FOR SEQ ID NO: 128:

(i) SEQUENCE CHARACTERISTICS:
         (A) LENGTH: 14 base pairs
         (B) TYPE: nucleic acid
         (C) STRANDEDNESS: single
         (D) TOPOLOGY: linear (ii) MOLECULE TYPE: other nucleic acid
         (A) DESCRIPTION:   /desc = "synthetic DNA"

(xi) SEQUENCE DESCRIPTION: SEQ ID NO: 128:

GGATGGCAGT AGCT                                                          14

(2) INFORMATION FOR SEQ ID NO: 129:

(i) SEQUENCE CHARACTERISTICS:
         (A) LENGTH: 14 base pairs
         (B) TYPE: nucleic acid
         (C) STRANDEDNESS: single
         (D) TOPOLOGY: linear (ii) MOLECULE TYPE: other nucleic acid
         (A) DESCRIPTION:   /desc = "synthetic DNA"

(xi) SEQUENCE DESCRIPTION: SEQ ID NO: 129:

ATTGGATGGC AGTA                                                          14

(2) INFORMATION FOR SEQ ID NO: 130:

(i) SEQUENCE CHARACTERISTICS:
         (A) LENGTH: 14 base pairs
         (B) TYPE: nucleic acid
         (C) STRANDEDNESS: single
         (D) TOPOLOGY: linear (ii) MOLECULE TYPE: other nucleic acid
         (A) DESCRIPTION:   /desc = "synthetic DNA"

(xi) SEQUENCE DESCRIPTION: SEQ ID NO: 130:

CAGGGTCTCG ATTG                                                          14
```

(2) INFORMATION FOR SEQ ID NO: 131:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 131:

ACCAGGGTCT CGAT                                                             14

(2) INFORMATION FOR SEQ ID NO: 132:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 132:

CCACCAGGGT CTCG                                                             14

(2) INFORMATION FOR SEQ ID NO: 133:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 133:

TGGAAGATGT CCAC                                                             14

(2) INFORMATION FOR SEQ ID NO: 134:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 134:

ATCTCATCAG GGTA                                                             14

(2) INFORMATION FOR SEQ ID NO: 135:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 135:

TCGATCTCAT CAGG                                                             14

(2) INFORMATION FOR SEQ ID NO: 136:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 136:

TACTCGATCT CATC                                              14

(2) INFORMATION FOR SEQ ID NO: 137:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 137:

GATGTACTCG ATCT                                              14

(2) INFORMATION FOR SEQ ID NO: 138:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 138:

ATGGCTTGAA GATG                                              14

(2) INFORMATION FOR SEQ ID NO: 139:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 139:

CAGGATGGCT TGAA                                              14

(2) INFORMATION FOR SEQ ID NO: 140:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 140:

CACAGGATGG CTTG                                              14

(2) INFORMATION FOR SEQ ID NO: 141:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 141:

CACACAGGAT GGCT                                                          14

(2) INFORMATION FOR SEQ ID NO: 142:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 142:

GGCACACAGG ATGG                                                          14

(2) INFORMATION FOR SEQ ID NO: 143:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 143:

GGGGCACACA GGAT                                                          14

(2) INFORMATION FOR SEQ ID NO: 144:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 144:

CAGCAGCCCC CGCA                                                          14

(2) INFORMATION FOR SEQ ID NO: 145:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 145:

ATTGCAGCAG CCCC                                                  14

(2) INFORMATION FOR SEQ ID NO: 146:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 146:

TCGTCATTGC AGCA                                                  14

(2) INFORMATION FOR SEQ ID NO: 147:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 147:

GGCCCTCGTC ATTG                                                  14

(2) INFORMATION FOR SEQ ID NO: 148:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 148:

TCCAGGCCCT CGTC                                                  14

(2) INFORMATION FOR SEQ ID NO: 149:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 149:

CACTCCAGGC CCTC                                                  14

(2) INFORMATION FOR SEQ ID NO: 150:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 150:

```
ACACACTCCA GGCC                                                        14

(2) INFORMATION FOR SEQ ID NO: 151:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION:    /desc = "synthetic DNA"

(xi) SEQUENCE DESCRIPTION: SEQ ID NO: 151:

TCCTCAGTGG GCACACAC                                                    18

(2) INFORMATION FOR SEQ ID NO: 152:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION:    /desc = "synthetic DNA"

(xi) SEQUENCE DESCRIPTION: SEQ ID NO: 152:

TCCTCAGTGG GCACAC                                                      16

(2) INFORMATION FOR SEQ ID NO: 153:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:    /desc = "synthetic DNA"

(xi) SEQUENCE DESCRIPTION: SEQ ID NO: 153:

TCCTCAGTGG GCAC                                                        14

(2) INFORMATION FOR SEQ ID NO: 154:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:    /desc = "synthetic DNA"

(xi) SEQUENCE DESCRIPTION: SEQ ID NO: 154:

TGGTGATGTT GGAC                                                        14

(2) INFORMATION FOR SEQ ID NO: 155:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION:    /desc = "synthetic DNA"
```

```
     (xi) SEQUENCE DESCRIPTION: SEQ ID NO: 155:

TGAGGTTTGA TCCG                                                         14

(2) INFORMATION FOR SEQ ID NO: 156:

(i) SEQUENCE CHARACTERISTICS:
         (A) LENGTH: 12 base pairs
         (B) TYPE: nucleic acid
         (C) STRANDEDNESS: single
         (D) TOPOLOGY: linear (ii) MOLECULE TYPE: other nucleic acid
         (A) DESCRIPTION:   /desc = "synthetic DNA"

(xi) SEQUENCE DESCRIPTION: SEQ ID NO: 156:

GAGGTTTGAT CC                                                           12

(2) INFORMATION FOR SEQ ID NO: 157:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: other nucleic acid
         (A) DESCRIPTION:   /desc = "synthetic DNA"

(xi) SEQUENCE DESCRIPTION: SEQ ID NO: 157:

AGGTTTGATC                                                              10

(2) INFORMATION FOR SEQ ID NO: 158:

(i) SEQUENCE CHARACTERISTICS:
         (A) LENGTH: 14 base pairs
         (B) TYPE: nucleic acid
         (C) STRANDEDNESS: single
         (D) TOPOLOGY: linear (ii) MOLECULE TYPE: other nucleic acid
         (A) DESCRIPTION:   /desc = "synthetic DNA"

(xi) SEQUENCE DESCRIPTION: SEQ ID NO: 158:

TCACATTTGT TGTG                                                         14

(2) INFORMATION FOR SEQ ID NO: 159:

(i) SEQUENCE CHARACTERISTICS:
         (A) LENGTH: 12 base pairs
         (B) TYPE: nucleic acid
         (C) STRANDEDNESS: single
         (D) TOPOLOGY: linear (ii) MOLECULE TYPE: other nucleic acid
         (A) DESCRIPTION:   /desc = "synthetic DNA"

(xi) SEQUENCE DESCRIPTION: SEQ ID NO: 159:

ACATTTGTTG TG                                                           12

(2) INFORMATION FOR SEQ ID NO: 160:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: other nucleic acid
         (A) DESCRIPTION:   /desc = "synthetic DNA"
```

(xi) SEQUENCE DESCRIPTION: SEQ ID NO: 160:

ATTTGTTGTG                                                                       10

(2) INFORMATION FOR SEQ ID NO: 161:

(i) SEQUENCE CHARACTERISTICS:
           (A) LENGTH: 14 base pairs
           (B) TYPE: nucleic acid
           (C) STRANDEDNESS: single
           (D) TOPOLOGY: linear (ii) MOLECULE TYPE: other nucleic acid
           (A) DESCRIPTION:    /desc = "synthetic DNA"

(xi) SEQUENCE DESCRIPTION: SEQ ID NO: 161:

GCTCTATCTT TCTT                                                                  14

(2) INFORMATION FOR SEQ ID NO: 162:

(i) SEQUENCE CHARACTERISTICS:
           (A) LENGTH: 12 base pairs
           (B) TYPE: nucleic acid
           (C) STRANDEDNESS: single
           (D) TOPOLOGY: linear (ii) MOLECULE TYPE: other nucleic acid
           (A) DESCRIPTION:    /desc = "synthetic DNA"

(xi) SEQUENCE DESCRIPTION: SEQ ID NO: 162:

GCTCTATCTT TC                                                                    12

(2) INFORMATION FOR SEQ ID NO: 163:

(i) SEQUENCE CHARACTERISTICS:
           (A) LENGTH: 10 base pairs
           (B) TYPE: nucleic acid
           (C) STRANDEDNESS: single
           (D) TOPOLOGY: linear (ii) MOLECULE TYPE: other nucleic acid
           (A) DESCRIPTION:    /desc = "synthetic DNA"

(xi) SEQUENCE DESCRIPTION: SEQ ID NO: 163:

GCTCTATCTT                                                                       10

(2) INFORMATION FOR SEQ ID NO: 164:

(i) SEQUENCE CHARACTERISTICS:
           (A) LENGTH: 14 base pairs
           (B) TYPE: nucleic acid
           (C) STRANDEDNESS: single
           (D) TOPOLOGY: linear (ii) MOLECULE TYPE: other nucleic acid
           (A) DESCRIPTION:    /desc = "synthetic DNA"

(xi) SEQUENCE DESCRIPTION: SEQ ID NO: 164:

ACATTTTTCT TGTC                                                                  14

(2) INFORMATION FOR SEQ ID NO: 165:

(i) SEQUENCE CHARACTERISTICS:
           (A) LENGTH: 14 base pairs
           (B) TYPE: nucleic acid
           (C) STRANDEDNESS: single
           (D) TOPOLOGY: linear (ii) MOLECULE TYPE: other nucleic acid (A) DESCRIPTION:   /desc = "synthetic DNA"

(xi) SEQUENCE DESCRIPTION: SEQ ID NO: 165:

GGCTTGTCAC ATTT                                                              14

(2) INFORMATION FOR SEQ ID NO: 166:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "synthetic DNA"

(xi) SEQUENCE DESCRIPTION: SEQ ID NO: 166:

CGCCTCGGCT TGTC                                                              14

(2) INFORMATION FOR SEQ ID NO: 167:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "synthetic DNA"

(xi) SEQUENCE DESCRIPTION: SEQ ID NO: 167:

CTCTGTCTTT CT                                                                12

(2) INFORMATION FOR SEQ ID NO: 168:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "synthetic DNA"

(xi) SEQUENCE DESCRIPTION: SEQ ID NO: 168:

CTCTCTCTTT CT                                                                12

(2) INFORMATION FOR SEQ ID NO: 169:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "synthetic DNA"

(xi) SEQUENCE DESCRIPTION: SEQ ID NO: 169:

TTGCTCTGTC TT                                                                12

(2) INFORMATION FOR SEQ ID NO: 170:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: other nucleic acid
        (A) DESCRIPTION:  /desc = "synthetic DNA"

(xi) SEQUENCE DESCRIPTION: SEQ ID NO: 170:

TTGCTCTCTC TT                                                          12

(2) INFORMATION FOR SEQ ID NO: 171:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  /desc = "synthetic DNA"

(xi) SEQUENCE DESCRIPTION: SEQ ID NO: 171:

GCTCTGTCTT TC                                                          12

(2) INFORMATION FOR SEQ ID NO: 172:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  /desc = "synthetic DNA"

(xi) SEQUENCE DESCRIPTION: SEQ ID NO: 172:

GCTCTCTCTT TC                                                          12

(2) INFORMATION FOR SEQ ID NO: 173:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  /desc = "synthetic DNA"

(xi) SEQUENCE DESCRIPTION: SEQ ID NO: 173:

TGCTCTGTCT TT                                                          12

(2) INFORMATION FOR SEQ ID NO: 174:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  /desc = "synthetic DNA"

(xi) SEQUENCE DESCRIPTION: SEQ ID NO: 174:

TGCTCTCTCT TT                                                          12

(2) INFORMATION FOR SEQ ID NO: 175:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: other nucleic acid
         (A) DESCRIPTION:   /desc = "synthetic DNA"

(xi) SEQUENCE DESCRIPTION: SEQ ID NO: 175:

GCTCTGTCTT TCT                                                          13

(2) INFORMATION FOR SEQ ID NO: 176:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: other nucleic acid
         (A) DESCRIPTION:   /desc = "synthetic DNA"

(xi) SEQUENCE DESCRIPTION: SEQ ID NO: 176:

GCTCTCTCTT TCT                                                          13

(2) INFORMATION FOR SEQ ID NO: 177:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: other nucleic acid
         (A) DESCRIPTION:   /desc = "synthetic DNA"

(xi) SEQUENCE DESCRIPTION: SEQ ID NO: 177:

TTGCTCTGTC TTT                                                          13

(2) INFORMATION FOR SEQ ID NO: 178:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: other nucleic acid
         (A) DESCRIPTION:   /desc = "synthetic DNA"

(xi) SEQUENCE DESCRIPTION: SEQ ID NO: 178:

TTGCTCTCTC TTT                                                          13

(2) INFORMATION FOR SEQ ID NO: 179:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: other nucleic acid
         (A) DESCRIPTION:   /desc = "synthetic DNA"

(xi) SEQUENCE DESCRIPTION: SEQ ID NO: 179:

TGCTCTGTCT TTC                                                          13

(2) INFORMATION FOR SEQ ID NO: 180:

(i) SEQUENCE CHARACTERISTICS:
        (A) LENGTH: 13 base pairs
        (B) TYPE: nucleic acid
        (C) STRANDEDNESS: single -continued

```
            (D) TOPOLOGY: linear (ii) MOLECULE TYPE: other nucleic acid
            (A) DESCRIPTION:    /desc = "synthetic DNA"

(xi) SEQUENCE DESCRIPTION: SEQ ID NO: 180:

TGCTCTCTCT TTC                                                                13

(2) INFORMATION FOR SEQ ID NO: 181:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: other nucleic acid
            (A) DESCRIPTION:    /desc = "synthetic DNA"

(xi) SEQUENCE DESCRIPTION: SEQ ID NO: 181:

TGCTCTGTCT TTCT                                                               14

(2) INFORMATION FOR SEQ ID NO: 182:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: other nucleic acid
            (A) DESCRIPTION:    /desc = "synthetic DNA"

(xi) SEQUENCE DESCRIPTION: SEQ ID NO: 182:

TGCTCTCTCT TTCT                                                               14

(2) INFORMATION FOR SEQ ID NO: 183:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: other nucleic acid
            (A) DESCRIPTION:    /desc = "synthetic DNA"

(xi) SEQUENCE DESCRIPTION: SEQ ID NO: 183:

TTGCTCTGTC TTTC                                                               14

(2) INFORMATION FOR SEQ ID NO: 184:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: other nucleic acid
            (A) DESCRIPTION:    /desc = "synthetic DNA"

(xi) SEQUENCE DESCRIPTION: SEQ ID NO: 184:

TTGCTCTCTC TTTC                                                               14

(2) INFORMATION FOR SEQ ID NO: 185:

(i) SEQUENCE CHARACTERISTICS:
            (A) LENGTH: 11 base pairs
            (B) TYPE: nucleic acid
```

```
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 185:

GCTCTCTCTT T                                                              11
```